United States Patent
Caille et al.

(10) Patent No.: US 9,263,680 B2
(45) Date of Patent: Feb. 16, 2016

(54) CROSSLINKABLE ARYLAMINE COMPOUNDS

(71) Applicant: SOLVAY SA, Brussels (BE)

(72) Inventors: Jean Raphael Caille, Namur (BE); Jonathan Maunoury, Brussels (BE)

(73) Assignee: SOLVAY SA, Brussels (BG)

( * ) Notice: Subject to any disclaimer, the term of this patent is extended or adjusted under 35 U.S.C. 154(b) by 0 days.

(21) Appl. No.: 14/369,454

(22) PCT Filed: Dec. 20, 2012

(86) PCT No.: PCT/EP2012/076301
§ 371 (c)(1),
(2) Date: Jun. 27, 2014

(87) PCT Pub. No.: WO2013/098175
PCT Pub. Date: Jul. 4, 2013

(65) Prior Publication Data
US 2015/0094437 A1 Apr. 2, 2015

(30) Foreign Application Priority Data
Dec. 28, 2011 (EP) ..................... 11010251

(51) Int. Cl.
H01L 51/00 (2006.01)
C07C 211/54 (2006.01)
(Continued)

(52) U.S. Cl.
CPC ............ *H01L 51/004* (2013.01); *C07C 211/54* (2013.01); *C07C 211/58* (2013.01);
(Continued)

(58) Field of Classification Search
None
See application file for complete search history.

(56) References Cited

FOREIGN PATENT DOCUMENTS

WO WO 2005049689 A2 * 6/2005
WO WO 2012003485 A2 * 1/2012

Primary Examiner — Vu A Nguyen

(57) ABSTRACT

Arylamine compounds comprising an arylamine core and at least one addition-polymerizable group X selected from the group consisting of formula (A); said addition polymerizable group attached to one ring of the arylamine core through a spacer of general formula (1): $C(R^1R^2)$—$(C(R^3R^4))_m$; wherein, $R^1$ and $R^2$, independent of one another, each represent a $C_1$-$C_8$ alkyl group or an aryl group of from 5 to 30 carbon atoms, $R^3$ and $R^4$, independent of one another, are hydrogen, a $C_1$ to $C_8$ alkyl group or an aryl group of from 5 to 30 carbon atoms and m is an integer of from 0 to 6, or through a fluorene subunit of general formulae (2) or (3); wherein $R^5$ represents hydrogen, $C_1$ to $C_8$-alkyl, or $C_5$ to $C_{30}$ aryl, and $R^6$ and $R^7$, independently of one another represent $C_1$ alkylene or a $C_5$ to $C_{30}$ arylene group, provided that $R^6$ and $R^7$ both carry an addition-polymerizable group X and $R^5$ is not hydrogen if $R^6$ is methylene.

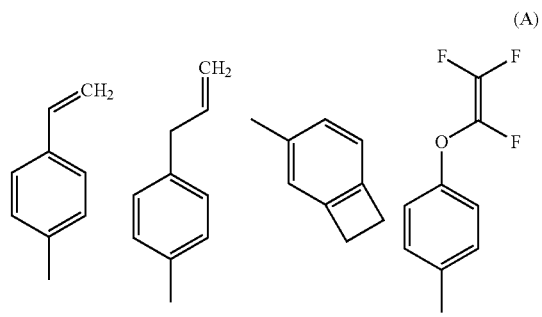

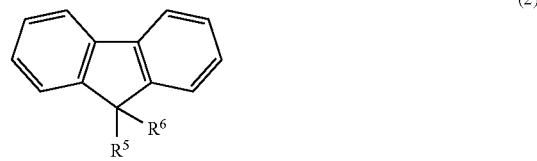

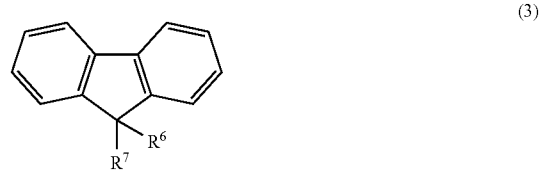

13 Claims, 2 Drawing Sheets

Structure of the OLED devices used in Comparative Example 3 and Device Examples 4 and 5

(51) Int. Cl.
*C07C 211/58* (2006.01)
*C07C 211/61* (2006.01)
*C07D 209/86* (2006.01)
*H01L 51/50* (2006.01)

(52) U.S. Cl.
CPC ............ *C07C211/61* (2013.01); *C07D 209/86* (2013.01); *H01L 51/006* (2013.01); *H01L 51/0059* (2013.01); *H01L 51/0061* (2013.01); *H01L 51/0072* (2013.01); *H01L 51/5012* (2013.01); *H01L 51/5056* (2013.01)

Figure 1. Structure of the OLED devices used in Comparative Example 3 and Device Examples 4 and 5
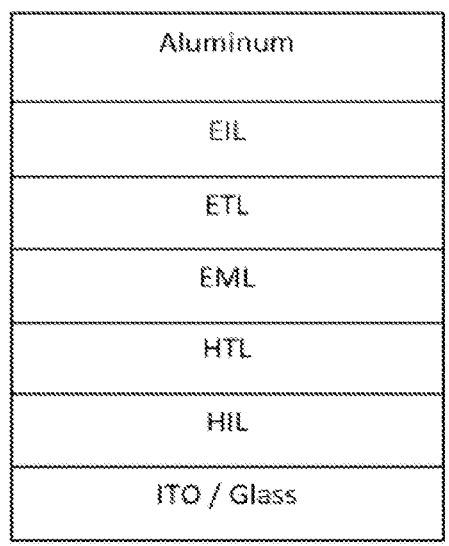

Figure 2. J-V characteristics of Comparative Example 3 (HTM1) and device Examples 4 (XLVI) and 5 (XLVII)
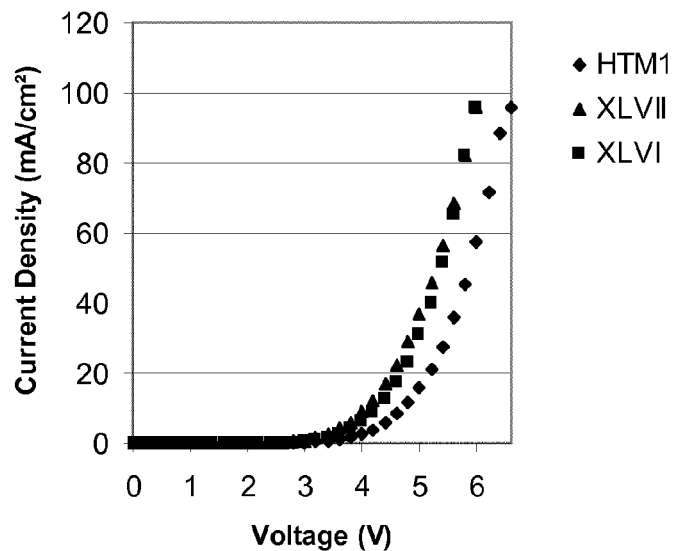
Figure 3. Lifetime data for devices of Comparative Example 3 and device Examples 4 (XLVI) and 5 (XLVII) ($L_0$ = 8000 cd/m²)
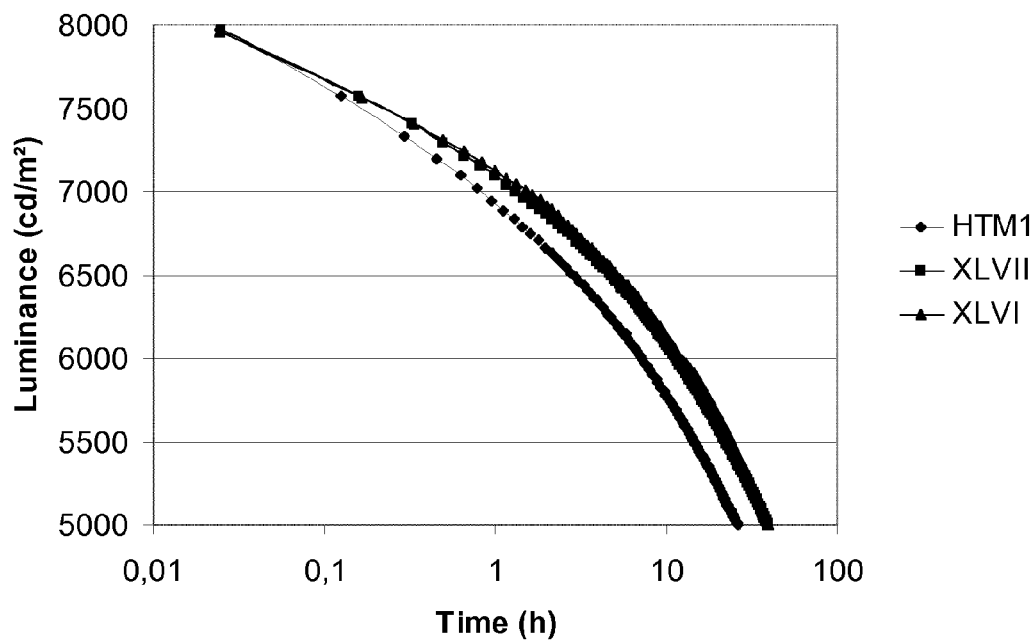

CROSSLINKABLE ARYLAMINE COMPOUNDS

This application is a U.S. national phase entry under 35 U.S.C. §371 of International Application No. PCT/EP2012/076301, filed on Dec. 20, 2012, which claims priority to European Application No. 11010251.4, filed on Dec. 28, 2011, the entirety of all of which is being incorporated herein by reference for all purposes.

The present invention relates to novel crosslinkable arylamine compounds useful for the manufacture of organic electronic devices.

Organic electronic devices typically comprise one or more semiconductive layers between electrodes.

For a number of reasons multilayer devices have been found to be advantageous especially in the field of Organic Light Emitting Diodes (OLED) as this allows to optimize the performance and efficiency of the device.

One challenge in the synthesis of multilayer devices is to avoid the interfacial mixing between different layers which is detrimental for lifetime and efficiency of the device. This is especially important when applying the economically most preferred solution process or the vapour deposition process, where different layers are sequentially applied onto the substrate. As the layer materials are often soluble in organic solvents, application of a subsequent layer out of solution leads to changes in the structure of the previous layer which is undesirable.

One possibility to overcome this issue is to modify a layer after it has been applied in a manner that the deposition of subsequent layers will not affect its integrity or composition.

One possibility is the use of so called orthogonal solvent systems for the application of sequential layers. Orthogonal solvent system means that for applying a subsequent layer a solvent system is used in which the previously applied layer is insoluble (i.e. has a very low solubility). This limits, however, the materials which can be used and optimum design of the device might be severely limited.

Crosslinking of a layer after it has been applied is another possibility to overcome the problem. After crosslinking the layer normally is no longer soluble and the structure and composition is no longer affected by the application of subsequent layers.

Jen et al, J. Mater. Chem. 2008, 18, 4495-4509 discloses crosslinkable hole transport materials for solution processed polymer light emitting diodes. Arylamine compounds having trifluorovinylether or styryl groups as crosslinkable groups are disclosed in Schemes 4 to 6 of the reference. The crosslinkable groups are attached to the electronically active core of the material via a —$CH_2$—O bridge or spacer.

Marder et al., Chem. Mat. Rev. 2011, 23, 658-681, provides an overview on approaches to solution processed multilayer OLED based on cross-linking. Various cross-linking chemistries are described, including siloxanes, styrenes, trifluorovinyl ethers, cinnamates and chalcones and oxetanes. Various aryl amine compounds are disclosed, all of which have the crosslinkable groups attached to the electronically active core of the aryl amine either directly or via a $CH_2$—O— spacer.

Jen et al., Chem. Mater. 2008, 20, 413-422 describes arylamine compounds with crosslinkable styryl groups which are attached to the electronically active core of the molecule via a $CH_2$—O— spacer again.

WO 2005/049689 describes cross-linkable substituted fluorine compounds for use especially in electroluminiscent devices. The compounds claimed have the structure

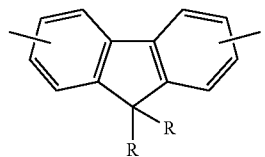

wherein at least one of the substituents R is a crosslinkable group. According to claim 4 benzo-3,4-cyclobutan-1-yl and p-vinylbenzyl. i.e. a styrene group attached via a CH2 group to the 9 or 9' position of the fluorenyl structure. Arylamines comprising such groups are not expressly disclosed.

WO 2005/049548 discloses arylamines with fluorenyl groups to which crosslinking groups are attached:

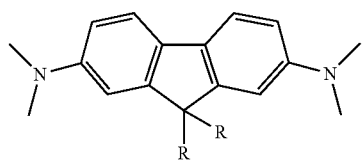

wherein R again is a crosslinkable group including benzo-3,4-cyclobutan-1-yl and p-vinylbenzyl. The only working example given in this document comprises a styryl group attached via a $CH_2$—O spacer.

WO 2006/043070 discloses arylamine compounds

Y-Ar1-N(Ar-Sp-X)-Ar2-N(Ar)-Ar1-Y' where Sp is an optional spacer and X is a crosslinkable group. Styryl and benzocyclobutane are mentioned as crosslinking groups and the spacer may be an alkylene group, in particular in combination with a benzocyclobutane crosslinking group. None of the compounds disclosed contains a spacer Sp; the crosslinkable group is always directly attached to the electronically active core of the arylamine.

The arylamine compounds described in the prior art comprising crosslinkable groups attached directly or via a spacer $CH_2$—O— to the electronically active core of the arylamine are not fully satisfactory in terms of stability of the devices containing such compounds as one of multiple layers. Accordingly there still exists a need for arylamine compounds comprising crosslinkable groups for use in multilayered OLED which on one hand are easily crosslinkable to facilitate the deposition of multiple layers on one hand and provide devices having satisfactory lifetime and efficiency on the other hand.

Thus, it was an object of the present invention to provide arylamine compounds providing improvements over the prior art compounds.

This object is achieved with the arylamine compounds in accordance with claim 1.

The arylamine compounds in accordance with the present invention comprise an arylamine core and at least one addition-polymerizable group X selected from the group consisting of

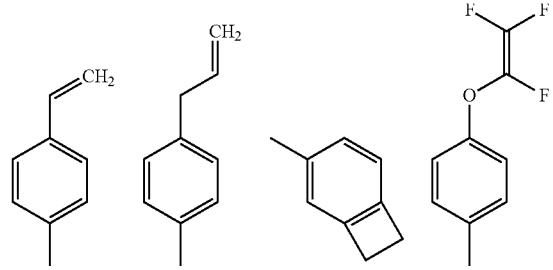

said addition polymerizable group attached to one ring of the arylamine core through a spacer of general formula (1)

$$C(R^1R^2)-(C(R^3R^4))m \quad (1)$$

wherein

R¹ and R², independent of one another, each represent a C₁-C₈ alkyl group or an aryl group of from 5 to 30 carbon atoms, R³ and R⁴, independent of one another, are hydrogen, a C₁ to C₈ alkyl group or an aryl group of from 5 to 30 carbon atoms and m is an integer of from 0 to 20, or through a fluorene subunit of general formulae (2) or (3)

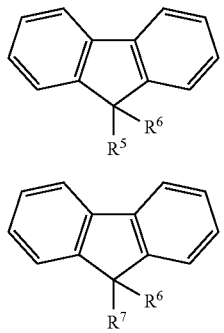

wherein

R⁵ represents hydrogen, C₁ to C₈-alkyl, or C₅ to C₃₀ aryl, and

R⁶ and R⁷, independently of one another, represent C₁ alkylene or a C₅ to C₃₀ arylene group, provided that R⁶ and R⁷ both carry an addition-polymerizable group X and R⁵ is not hydrogen if R⁶ is methylene.

Preferred embodiments of the present invention are set forth in the dependent claims and the specification hereinafter.

The arylamine compounds in accordance with the present invention comprise an arylamine core. When used herein, the term arylamine core generally denotes a structural element where aryl groups are attached to one or more nitrogen atoms.

Generally, an arylamine core can be depicted as NAr¹Ar²Ar³ wherein Ar¹, Ar² and Ar³, which may be the same or different, represents a substituted or unsubstituted C₅ to C₃₀ aryl- or a substituted or unsubstituted C₂ to C₃₀ heteroaryl group. Preferred examples of aryl groups are phenyl, naphthyl and anthracenyl, especially phenyl or naphthyl. Preferred heteroaryl groups are five or six membered heteroaryl compounds comprising at least one heteroatom, preferably selected from O, N and S, particularly preferred the heteroaryl ring contains at least one nitrogen atom.

The term addition-polymerizable group, when used in the context of the present invention, denotes a group capable of undergoing an addition polymerization reaction, i.e. a reaction where a polymer is formed through a rearrangement of chemical bonds without the formation or split-off of low molecular weight compounds (contrary to groups polymerizing by condensation polymerization). Addition polymerizable groups may be polymerized thermally or by UV or visible radiation, depending on their chemical structure. The skilled person, based on his knowledge will select the appropriate addition-polymerizable group dependent on the intended method of polymerization and the desired properties of the polymers.

The arylamine compounds in accordance with the present invention comprise at least one addition polymerizable group which is attached to one ring of an arylamine core through a spacer or a fluorene group as more specifically defined hereinafter.

The spacer has the general formula C(R¹R²)—(C(R³R⁴))ₘ wherein R¹ and R², independent of one another, each represent a C₁-C₈ alkyl group or an aryl group of from 5 to 30 carbon atoms.

It has surprisingly been found that spacers having no hydrogen atoms at the carbon atom which is bound to the arylamine core provide a better stability when used in organic electronic devices compared to respective compounds bearing one or more hydrogen atoms at the respective carbon atom.

In accordance with a preferred embodiment of the present invention, the spacer of formula (1) is linked to the arylamine core through the carbon atom which bears substituents R¹ and R².

R³ and R⁴, independent of one another, are hydrogen, a C₁ to C₅ alkyl group or an aryl group of from 5 to 30 carbon atoms and m is an integer of from 0 to 20. In accordance with a preferred embodiment, R¹ and R² both represent a C₁ to C₄ alkyl group, particularly preferred a methyl group.

In accordance with another preferred embodiment, m is an integer of from 0 to 6, preferably of from 0 to 3 and particularly preferably m is 0 or an integer of from 1 to 3.

Alternatively, the addition polymerizable group may be attached to a ring of an arylamine core through a fluorene subunit of formula (2) or (3)

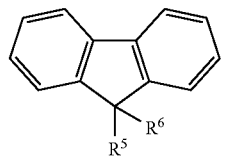

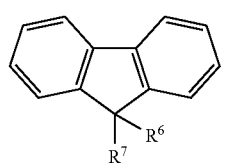

wherein R⁵ represents hydrogen, C₁ to C₈-alkyl, or C₅ to C₃₀ aryl, and

R⁶ and R⁷, independently of one another represent C₁ alkylene or a C₅ to C₃₀ arylene group, provided that R⁶ and R⁷ both carry an addition-polymerizable group X and R⁵ is not hydrogen if R⁶ is methylene.

According to a preferred embodiment of the present invention R⁵ is hydrogen or a C₁ to C₄ alkyl group, especially preferably a methyl group.

In accordance with another preferred embodiment both R⁶ and R⁷ are a methylene group (—CH₂—).

The term C₁-alkylene, as used herein, is intended to include CH₂ as well as methylene groups wherein one or both hydrogen atoms have been replaced by substituents, e.g. alkyl or alkoxy groups.

A first preferred class of arylamine compounds in accordance with the present invention is represented by compounds of general formula (4)

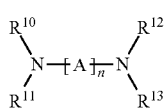

wherein at least one of A and R¹⁰ to R¹³ carries an addition-polymerizable group attached through a spacer of general formula (1) wherein A can have the same meaning as Ar¹ defined above; preferably A is selected from the group consisting of substituted or unsubstituted 5 to 7 membered aryl or heteroaryl rings, n is 1, 2 or 3 and R¹⁰ to R¹³ are unsubstituted or substituted C₅ to C₃₀ aryl or C₂ to C₃₀ heteroaryl rings as defined before for Ar¹.

In accordance with another preferred embodiment, the compounds of the present invention of formula (4) comprise a substituted or unsubstituted phenyl or naphthyl group.

The addition polymerizable group preferably comprises at least one unsaturated bond which may be polymerized by addition polymerization.

Vinyl groups are generally preferred as group X, particularly vinylphenyl (also commonly referred to as styryl or vinylphenyl).

The following specific examples of arylamine compounds (formulae I to XLV), individually, are preferred in accordance with the present invention, compounds XVII to XLV being especially preferred.

(I)

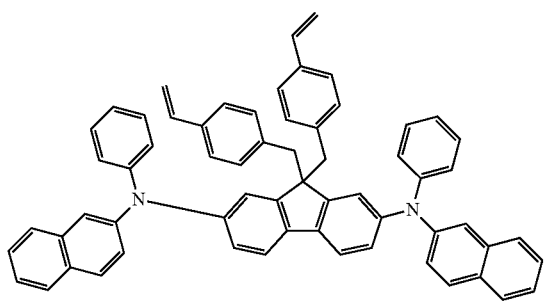

(II)

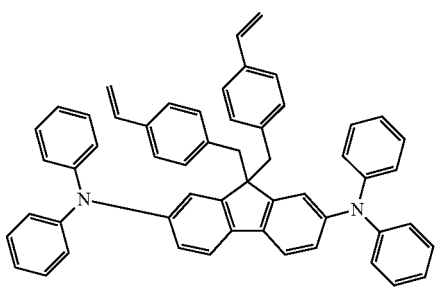

(III)

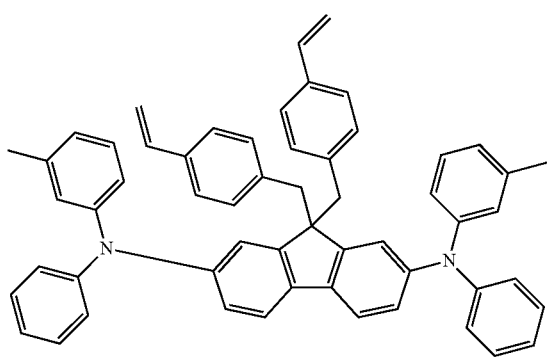

(IV)

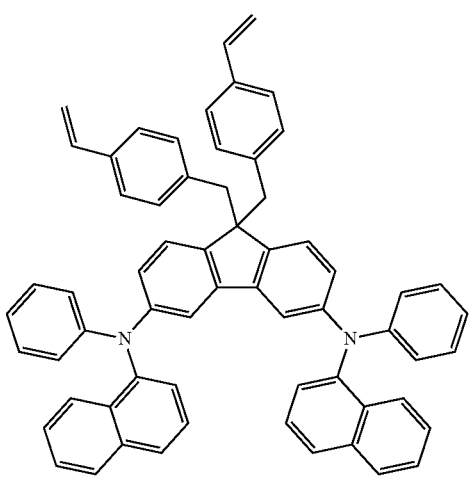

(V)

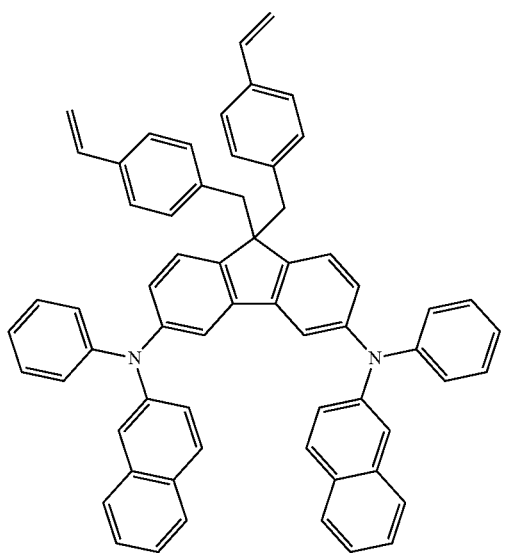

(VI)

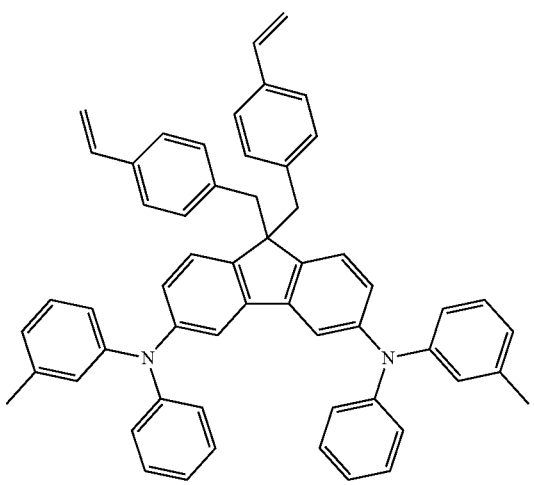

(VII)
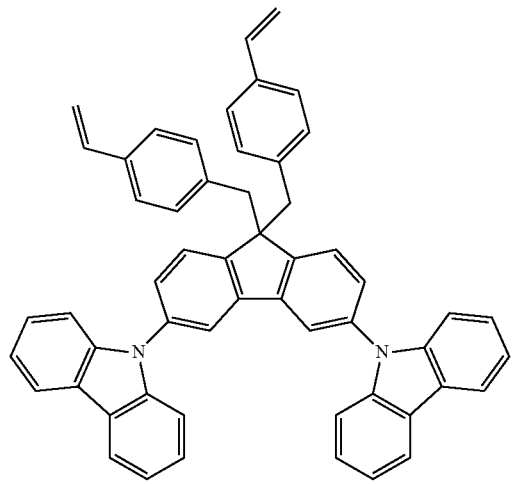
(VIII)
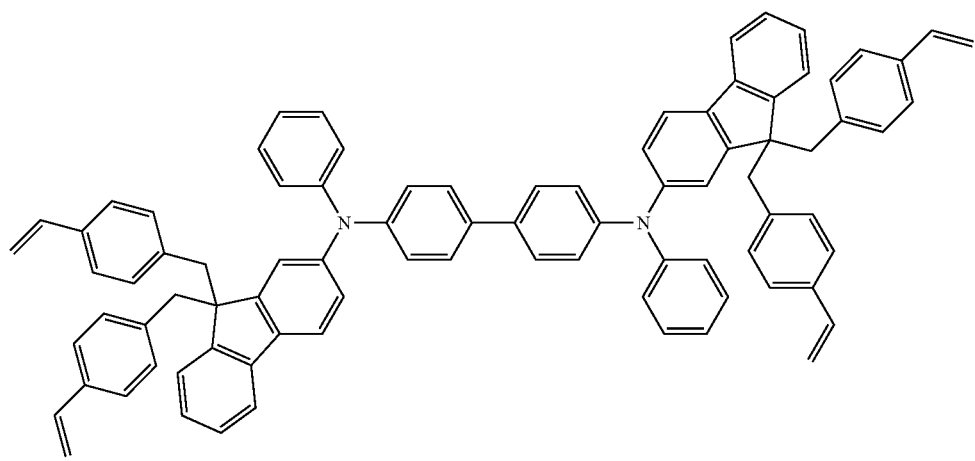
(IX)
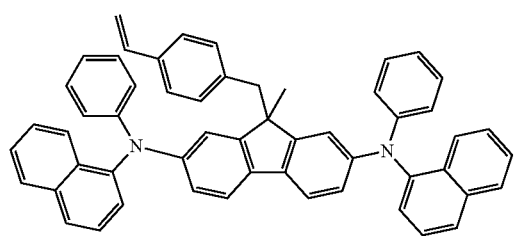
(X)
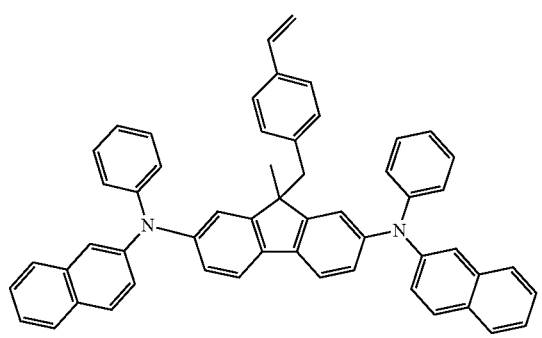

-continued
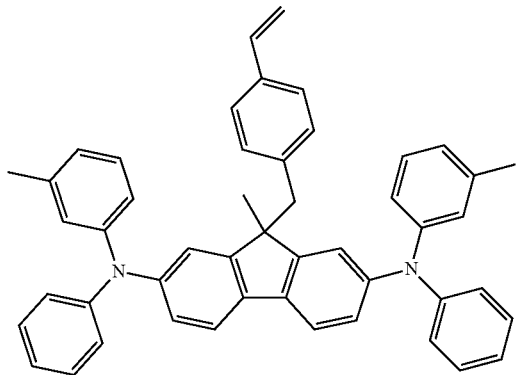
(XI)
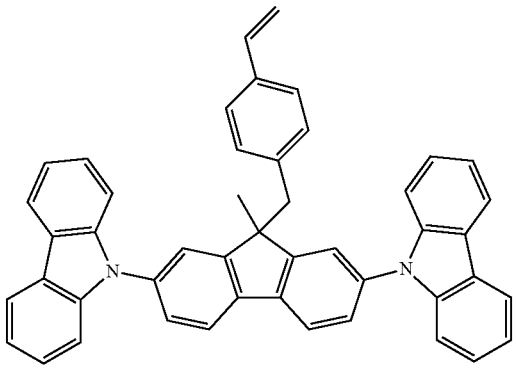
(XII)
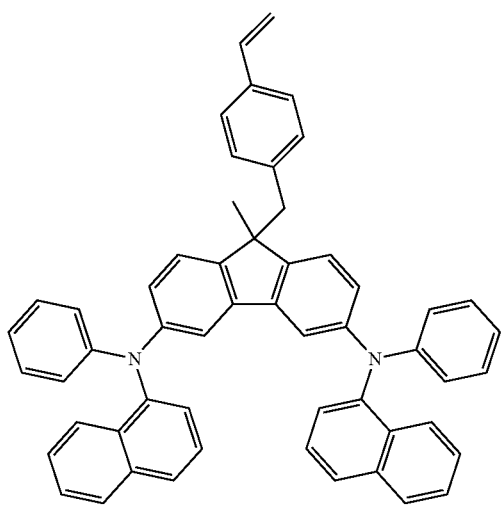
(XIII)
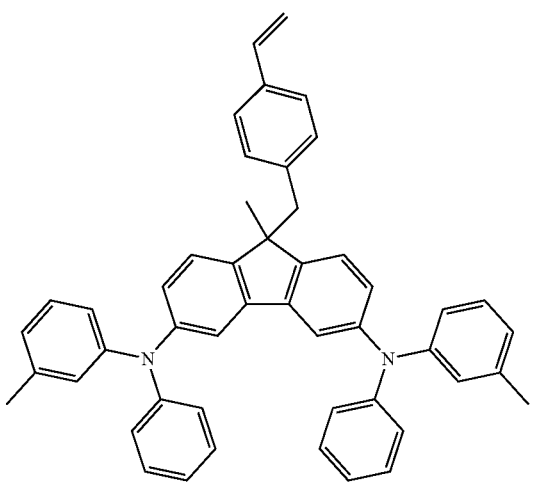
(XIV)
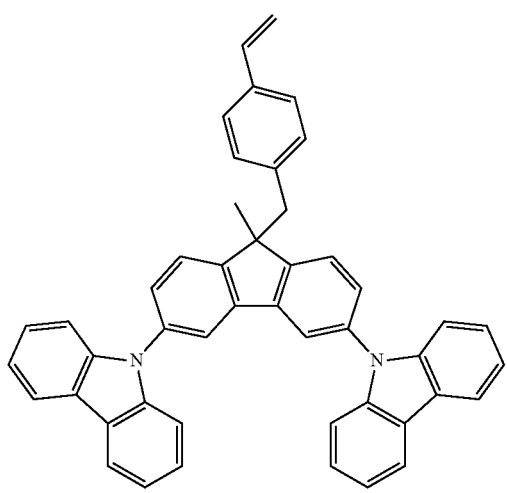
(XV)

(XVI)
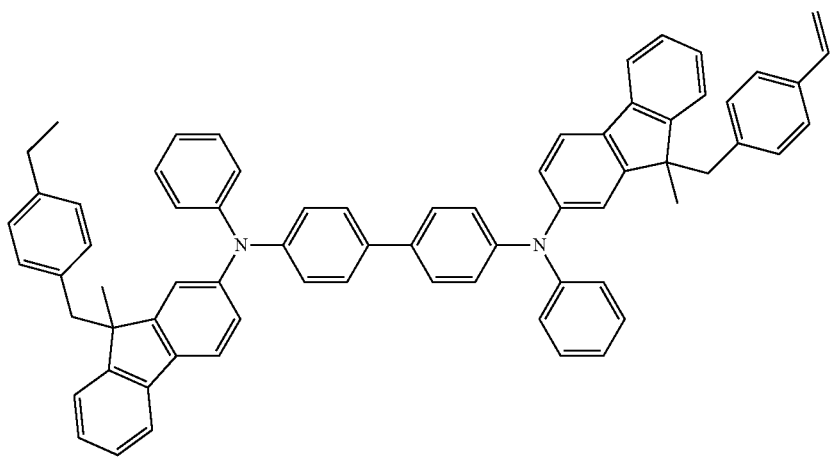
(XVII)
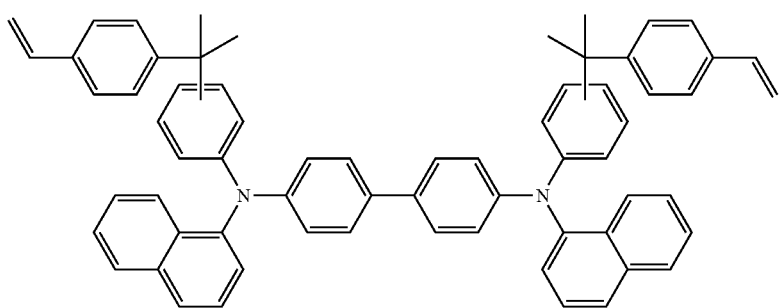
(XIX)
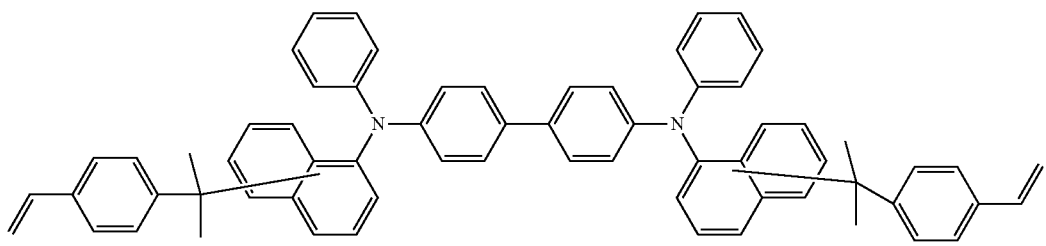
(XX)
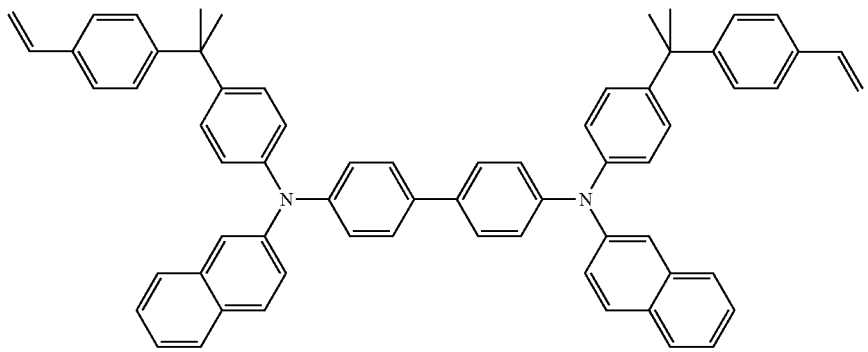

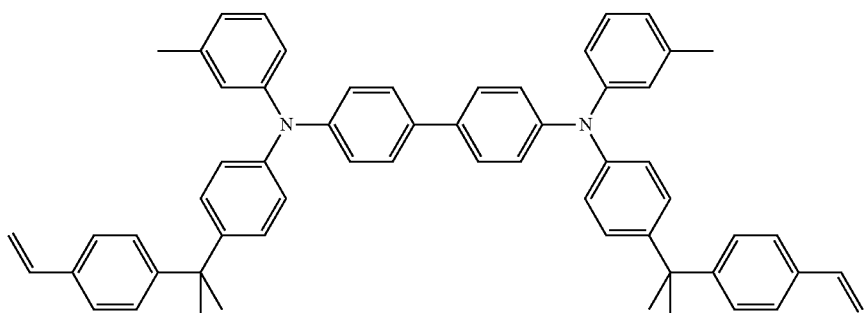
(XXI)
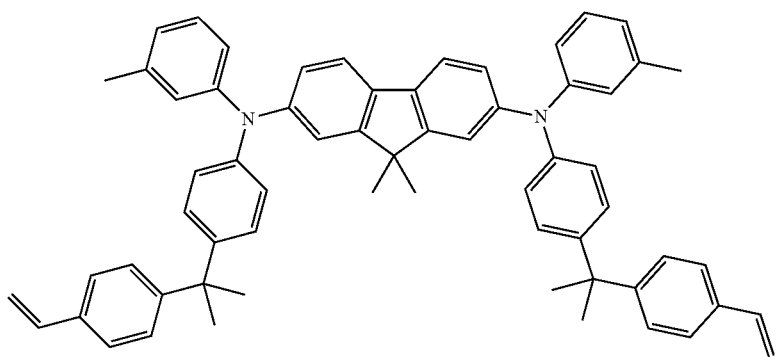
(XXII)
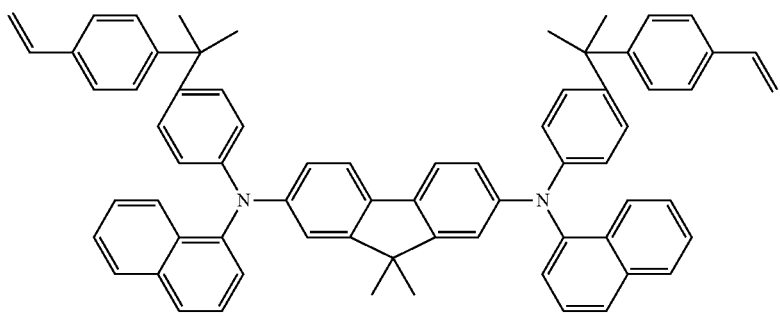
(XXIII)
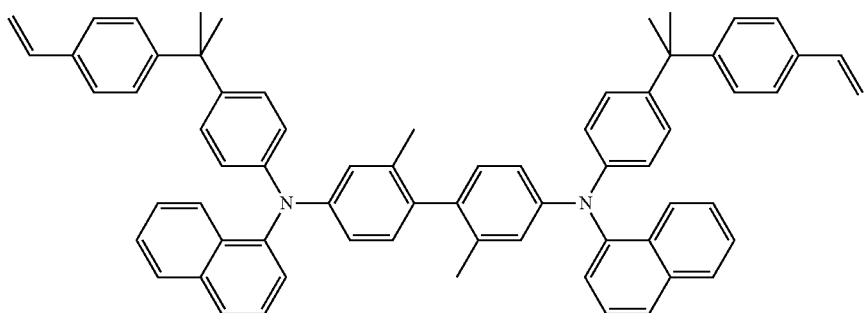
(XIV)

-continued
(XXV)
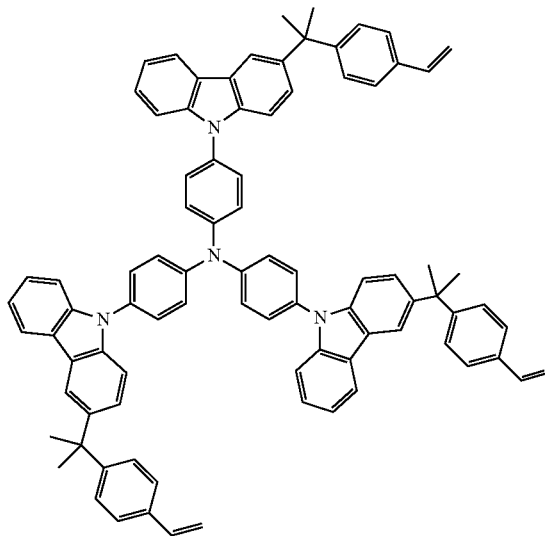
(XXVI)
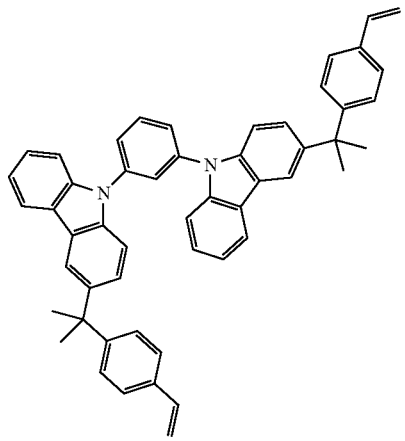
(XXVII)
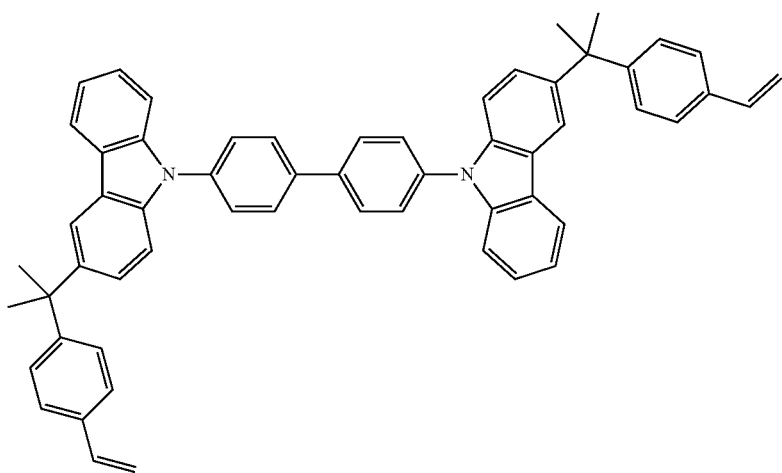
(XVIII)
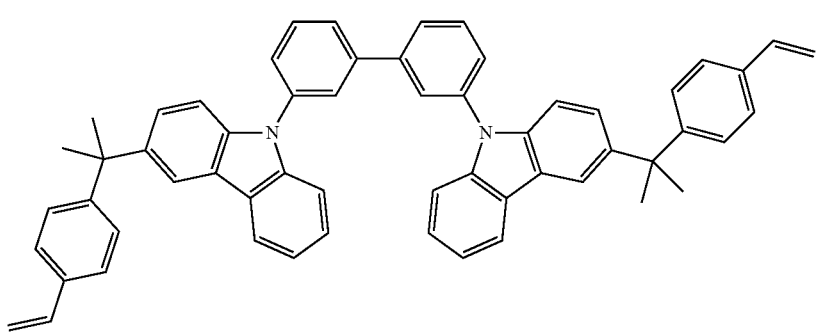

-continued
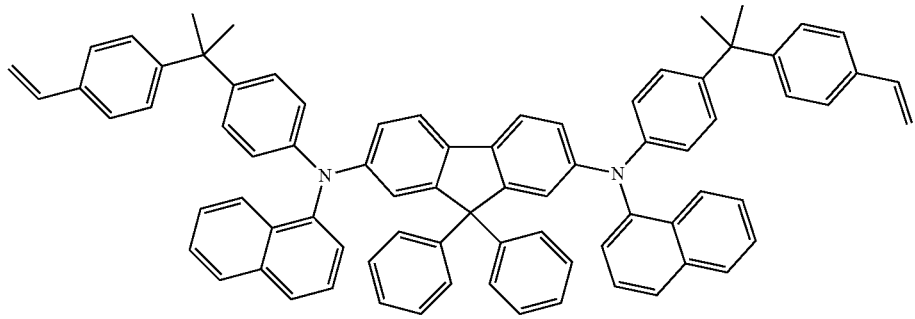
(XXIX)
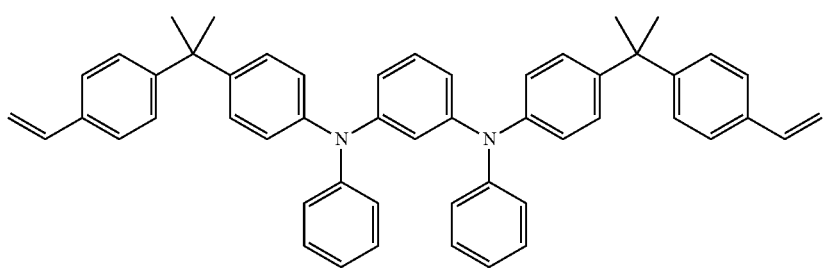
(XXX)
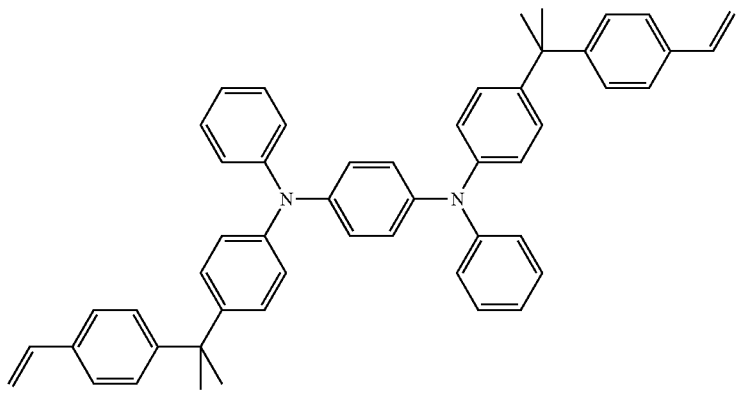
(XXXI)
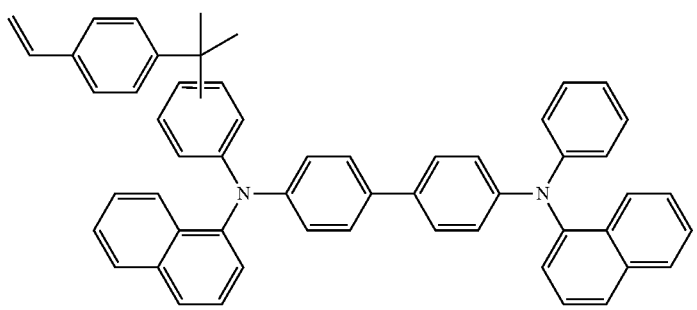
(XXXII)
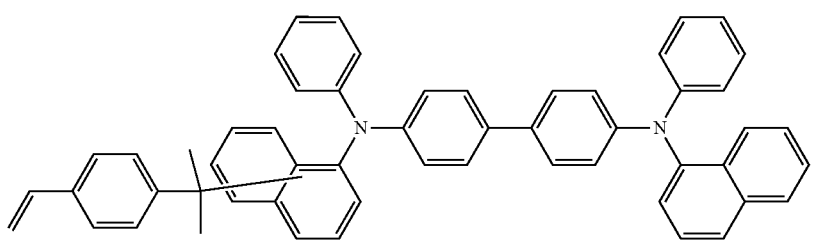
(XXXIII)

-continued
(XXXIV)
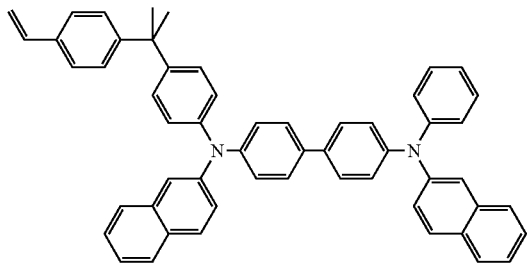
(XXXV)
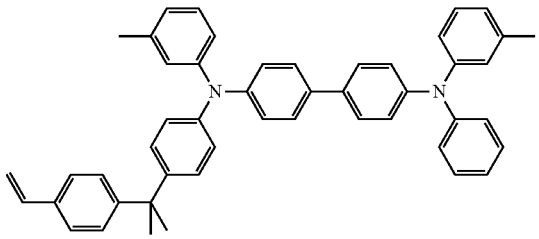
(XXXVI)
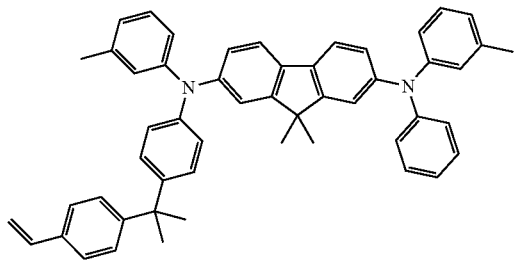
(XXXVII)
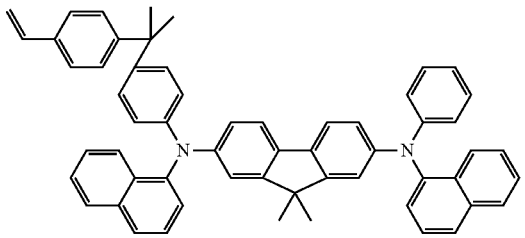
(XXXVIII)
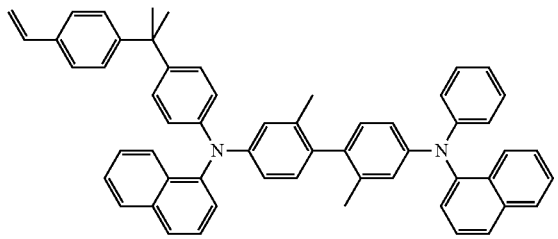
(XXXIX)
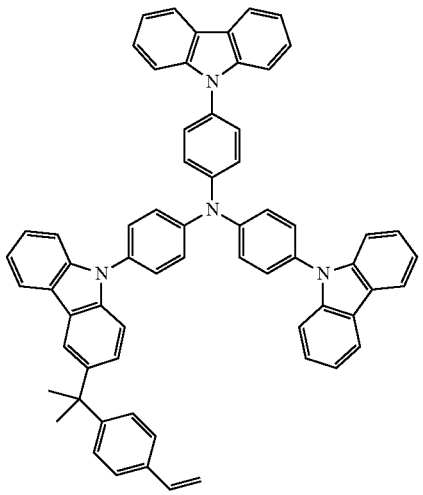
(XL)
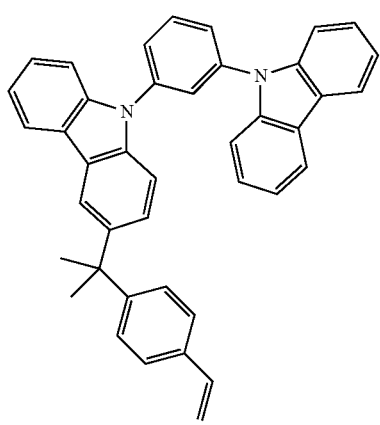
(XLI)
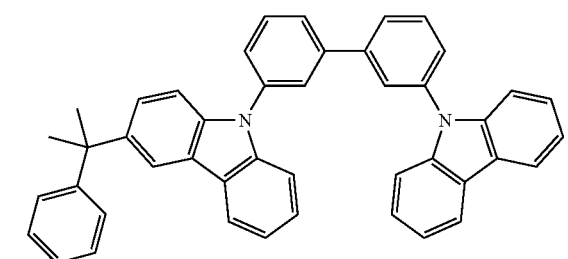

(XLII)
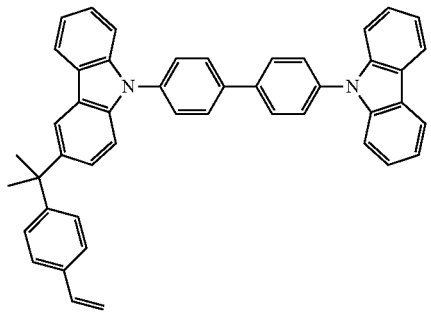

(XLIII)
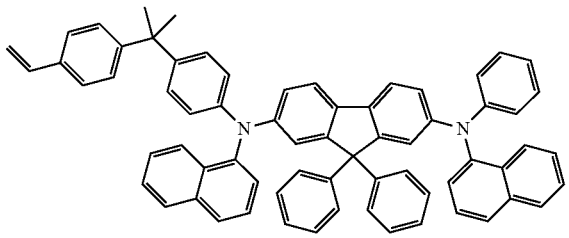

(XLIV)
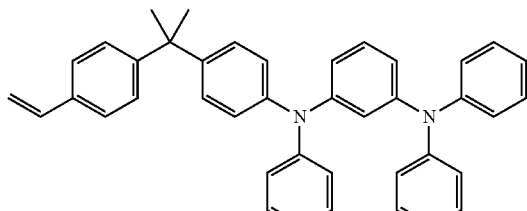

(XLV)
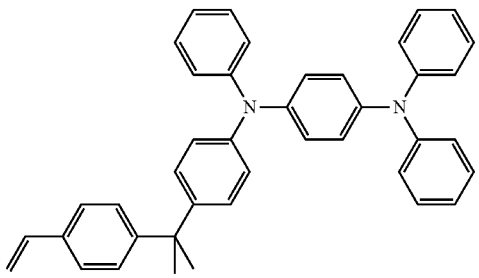

Two particularly preferred compounds in accordance with the present invention are compounds of formulae XLVI and XLVII The person skilled in the art will select the appropriate reaction conditions and reactants depending on the intended product.

(XLVI)
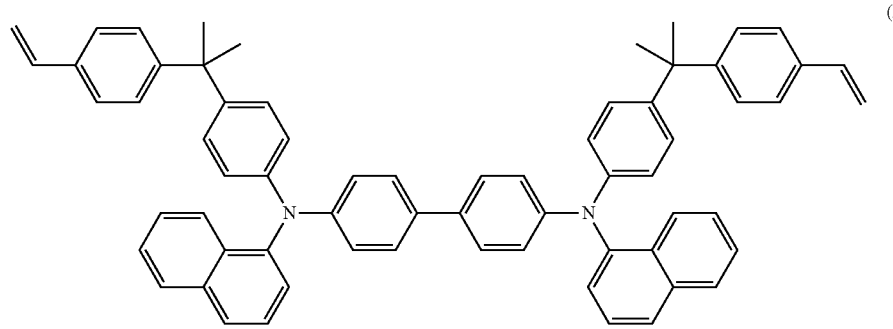

(XLVII)
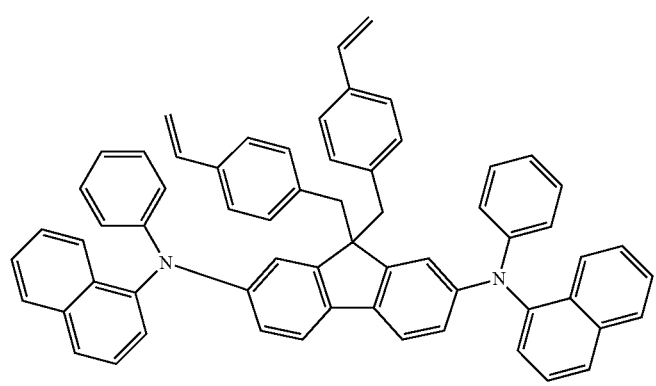

The compounds in accordance with the present invention can be synthesized in accordance with methods described in the literature and known to the person skilled in the art. Accordingly, there is no need for a detailed description here.

The compounds in accordance with the present invention may be used for the formation of any layer of a multi-layered organic electronic device, in particular an OLED stack (hole transport layer, electron transport layer, hole blocking layer etc.). The person skilled in the art will select the suitable compounds in accordance with the desired function of the layer.

With the compositions in accordance with the present invention, the crosslinking density of a film layer obtained from the inventive arylamine compounds can be finely controlled and several advantages may be obtained, e.g. lowering of the glass transition temperature which allows a better removal of solvent, a higher double bond conversion and a lower energy required for curing. Furthermore, shrinkage and film morphology are improved.

The arylamine compounds in accordance with the present invention are particularly suitable for the manufacture of hole transport layers in OLEDs and thus another embodiment of the present invention relates to the use of the compositions in accordance with the present invention for the manufacture of hole transport layers in OLEDs.

For practical reasons it is preferably to use arylamine compounds which are effective in achieving crosslinking at temperatures not detrimentally influencing the polymer formed.

Usually reaction temperatures for the desired crosslinking are in the range of from 150 to 250° C. and preferably compound b) is selected to achieve a desired degree of crosslinking at a temperature of not more than 220° C., in particular of not more than 200° C.

Finally a third embodiment of the present invention relates to polymers obtained from the arylamine compounds in accordance with the present invention.

The compounds in accordance with the present invention are particularly useful in the manufacture of multilayered OLED devices by solution processes or by vapour phase processes where the previously deposed layer has to be inert under the reaction conditions with the subsequent deposited layer to avoid undesired changes in the properties of the device. Solution and vapour phase processes for the manufacture of such multilayered organic electronic devices are known to the skilled person and described in the literature so that no detailed description is necessary here.

BRIEF DESCRIPTION OF THE DRAWINGS

FIG. 1 shows a schematic structure of OLED devices in accordance with comparative Example 3 and Examples 4 and 5.

FIG. 2 shows the J-V characteristics of comparative example 3 and examples 4 and 5, and FIG. 3 shows the lifetime data for devices of comparative example 3 and device examples 4 and 5

An OLED generally comprises:
a substrate, for example (but not limited to) glass, plastic, metal;
an anode, generally transparent anode, such as an indium-tin oxide (ITO) anode;
a hole injection layer (HIL) for example (but not limited to) PEDOT/PSS;
a hole transport layer (HTL);
an emissive layer (EML);
an electron transport layer (ETL);
an electron injection layer (EIL) such as LiF, $Cs_2CO_3$ and
a cathode, generally a metallic cathode, such as an Al layer.
A schematic structure of the devices of device examples 3 to 5 is given in FIG. 1.

EXAMPLES

Example 1

Synthesis of Compound XLVI

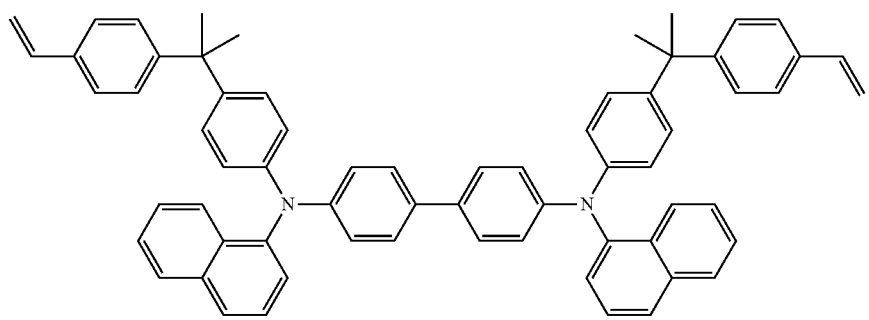 [SMILES: C=Cc1ccc(C(C)(C)c2ccc(N(c3ccc(-c4ccc(N(c5ccc(C(C)(C)c6ccc(C=C)cc6)cc5)c5cccc6ccccc56)cc4)cc3)c3cccc4ccccc34)cc2)cc1]

In a 250 ml 2 necked round-bottom flask equipped with a condenser and under argon were dissolved 5.3 g of N4,N4'-di(naphthalen-1-yl)-N4,N4'-diphenylbiphenyl-4,4'-diamine (NPD) and 4.2 g of 2(4-bromophenyl-2-propanol) in 65 ml of dichloromethane. Then 3.15 ml of $BF_3$, $Et_2O$ were added dropwise under stirring at room temperature. The reaction was monitored by thin layer chromatography (TLC). After completion, the reaction medium was filtered through a silica gel plug. The plug was rinsed by 25 ml of dichloromethane. After removal of the solvent under reduced pressure crude product was recovered and purified by flash chromatography over silica gel using a mixture of 50/50 v/v hexane/dichloro methane as the eluent. 8.1 g of pure N4,N4'-bis(4-(2-(4-bromophenyl)propan-2-yl)phenyl)-N4,N4'-di(naphthalen-1-yl)biphenyl-4,4'-diamine was obtained. Structure was confirmed by NMR.

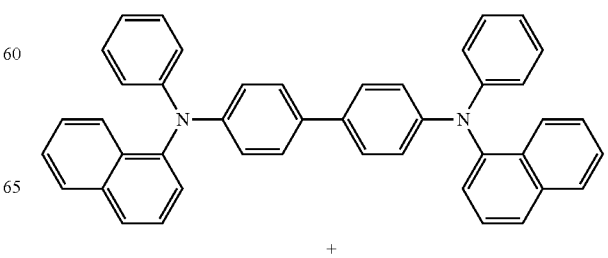

+

25

-continued

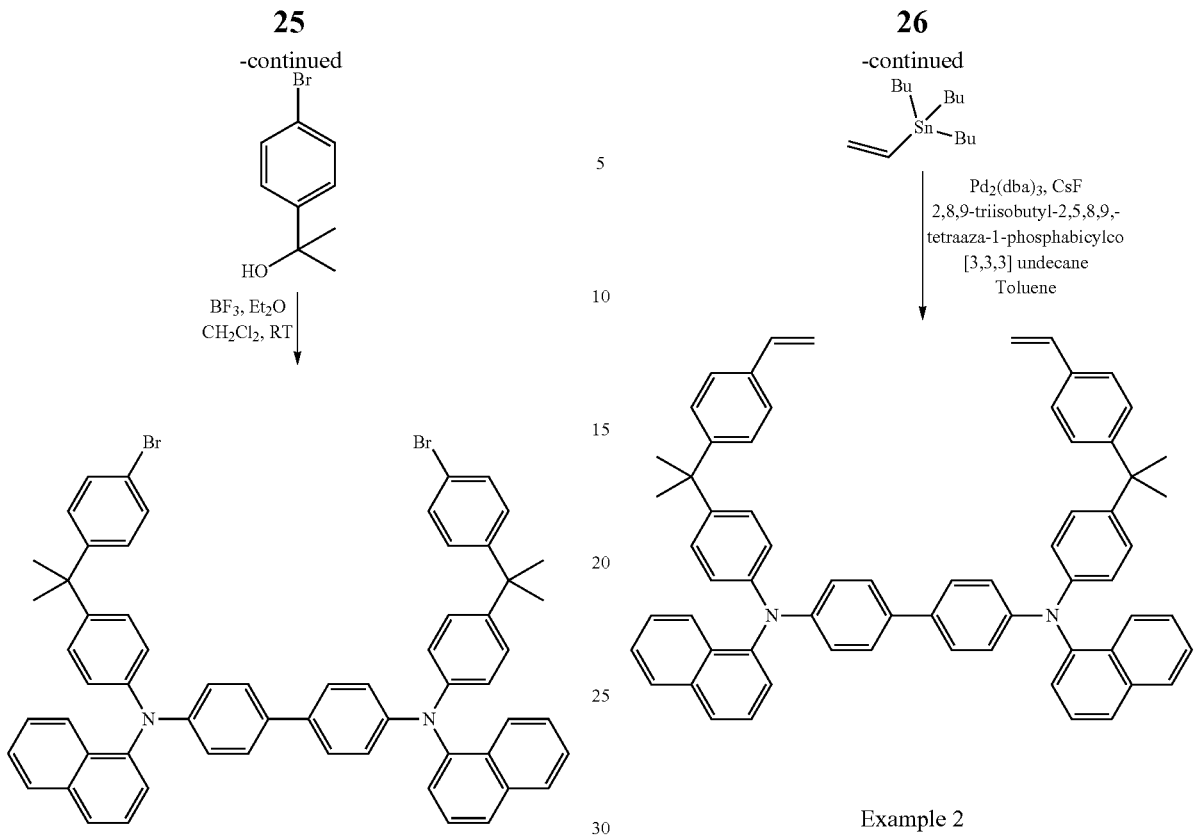

In a 250 ml 2 necked round-bottom flask equipped with a condenser and under argon were added 5.1 g of N4,N4'-bis (4-(2-(4-bromophenyl)propan-2-yl)phenyl)-N4,N4'-di (naphthalen-1-yl)biphenyl-4,4'-diamine, 3.34 g of CsF, 0.14 g of $Pd_2(dba)_3$ (dba denoting dibenzylidene acetone ligand). Then, 30 ml of dry THF, 3.3 ml of vinyltributyltin and 0.11 ml of 2,8,9-triisobutyl-2,5,8,9-tetraaza-1-phosphabicyclo[3,3,3]undecane were successively added with syringes. The reaction medium was heated to reflux and stirred during 50 h. After filtration through a plug of silica gel and removal of the solvent by distillation under reduced pressure a crude product was obtained. It was first purified by precipitation into methanol, recovered by filtration and purified again by flash chromatography onto silica gel using a 65/35 v/v mixture of Hexane/Toluene. 2.05 g of pure compound XLVI was obtained. Structure was confirmed by NMR.

26

-continued

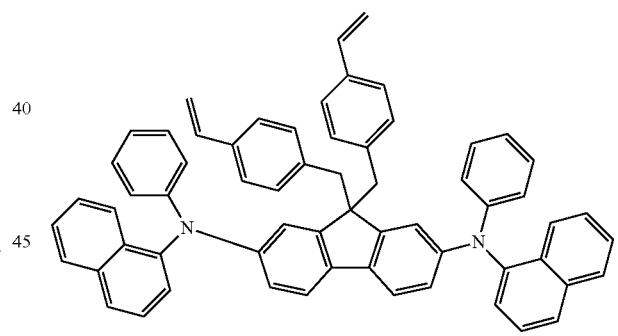

Example 2

Synthesis of Compound XLVII

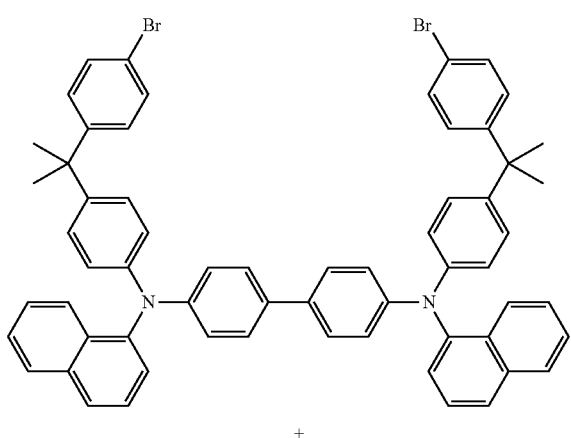

In a 500 ml three necked round-bottom flask equipped with a condenser were introduced 14.6 g of 2,7-dibromofluorene, 150 ml of potassium hydroxide (KOH) 2M, 150 ml of toluene and 2.9 ml of a 50 wt % solution of tetra-n-butyl ammonium bromide (TBAB) in water. Then 17.6 ml of p-vinylbenzyl-chloride were gently added under vigorous mechanical stirring. The reaction was stirred overnight at 80° C. and after cooling the organic layer was extracted and then washed with water until neutral pH. After drying of the organic phase onto $MgSO_4$, the solvent was removed by distillation under vacuum. A crude product was recovered which was purified by flash chromatography onto silica gel using a 20/80 v/v mixture of dichloro methane and hexane. 7.8 g of pure 2,7-dibromo-9,9-di(vinylbenzyl)fluorene were obtained. The structure was confirmed by NMR.

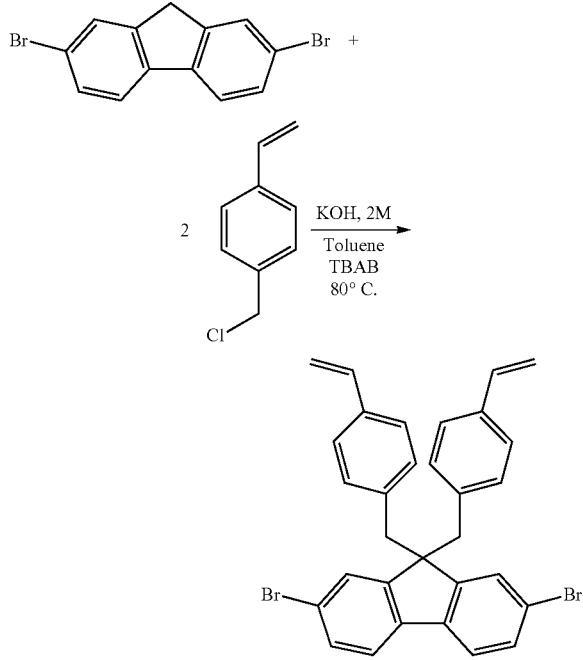

In an oven-dried three necked round-bottom flask under argon atmosphere were added 4.5 g of N-phenyl-1-napthylamine, 5.6 g of 2,7-dibromo-9,9-di(vinylbenzyl)fluorene, 4.7 g of KOt-Bu, 0.138 g of Pd(dba)$_2$ (dba representing dibenzylideneacetone) and 100 ml of dried toluene. Then 0.3 ml of a 1M solution of P(t-Bu)$_3$ in toluene were added and the reaction medium was stirred for 24 h at 80° C. After cooling the reaction medium was filtered through a 50 g of alumina plug. The plug was rinsed with 100 ml of toluene. Crude product was obtained after removal of toluene by distillation under vacuum and purified by flash chromatography onto silica gel using a 60/40 v/v hexane/toluene mixture. 2.1 g of pure compound XLVII were obtained. The structure was confirmed by NMR.

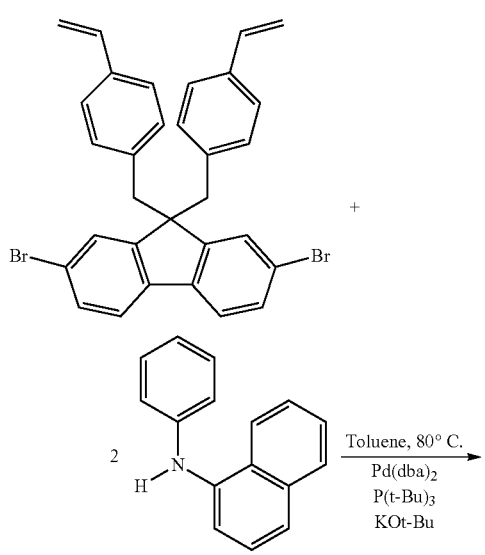

Device Examples

General Method for Device Manufacture

All devices were manufactured by a combination of high vacuum thermal evaporation and solution processing (spin-coating). The anode electrode was 120 nm of indium tin oxide (ITO). All devices were encapsulated with a glass lid sealed with an epoxy resin in a nitrogen glove box (<1 ppm of H$_2$O and O$_2$) immediately after fabrication, and a moisture getter was incorporated inside the package. The devices were characterized optically and electrically with a C9920-12 External Quantum Efficiency Measurement System from HAMAMATSU. EQE refers to external quantum efficiency expressed in %, while operational stability tests were done by driving the devices at continuous current at room temperature. LT$_{70}$ is a measure of lifetime and corresponds to the time for the light output to decrease to 70% of the initial value, when the device is driven at a constant current.

The OLED stack consisted of sequentially, from the ITO surface, 60 nm of a hole injection layer (HIL) of Plexcore OC AQ 1200 (a self-doping polymer, poly(thiophene-3-[2[(2-methoxyethoxy)ethoxy]-2,5-diyl), supplied by Plextronics Inc.)

deposited by spin-coating in air. Further fabrication step were carried out in a nitrogen glove box (<1 ppm of H$_2$O and O$_2$). The HIL was annealed on a hot plate at 180° C. for 20 min.

A hole transport layer (HTL) of 30 nm was deposited on top of the HIL by spin-coating a 1 wt % solution of HTM1 or Compound XLVI or Compound XLVII in toluene. The HTL was then annealed on a hot plate at 200° C. for 60 min.

Then a 20 nm layer of TCzMe doped with 20% of tris[4-methyl-2-phenylquinoline]iridium(III) [Ir(Mphq)$_3$] was deposited by vacuum-thermal evaporation as the emissive layer (EML). Then a 10 nm layer of bis(2-methyl-8-quinolinolate)-4-(phenylphenolato)aluminium (BAlq) was deposited by vacuum-thermal evaporation as the electron transport layer (ETL). Then, a 45 nm layer of BCP:Cs$_2$CO$_3$ 10% (BCP=2,9-dimethyl-4,7-diphenyl-1,10-phenanthroline) was deposited by vacuum-thermal evaporation as the electron injection layer (EIL). The cathode consisted of 50 nm of Al.

The device details and performance data are summarized in Table 1. As used herein, HTM1, Compound XLVI, Compound XLVII, TCzMe, Ir(Mphq)₃, BAlq and BCP have the following structures:
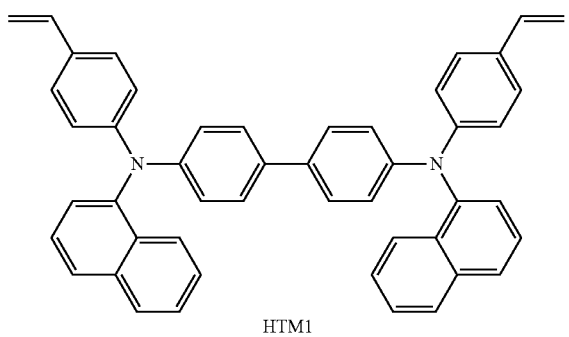
HTM1
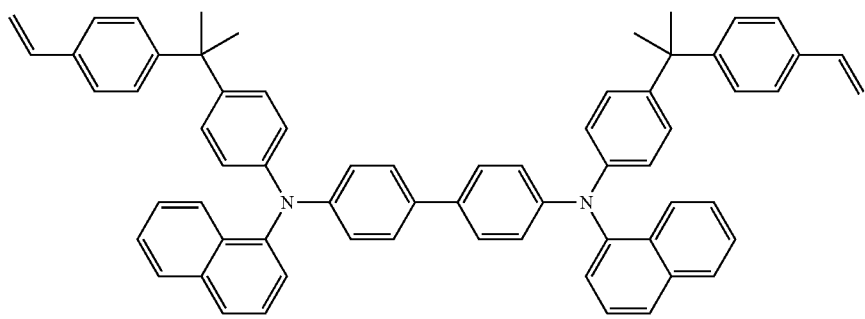
XLVI
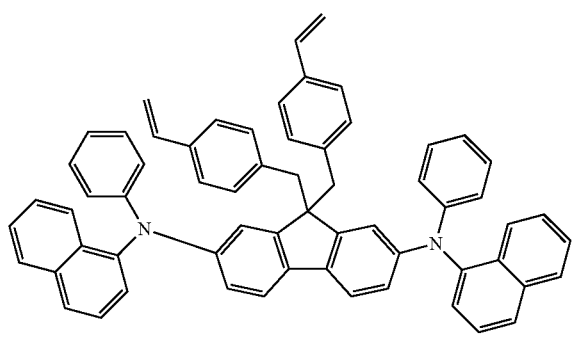 [SMILES: C=Cc1ccc(CC2(Cc3ccc(C=C)cc3)c3cc(N(c4ccccc4)c4cccc5ccccc45)ccc3-c3ccc(N(c4ccccc4)c4cccc5ccccc45)cc32)cc1]
XLVII
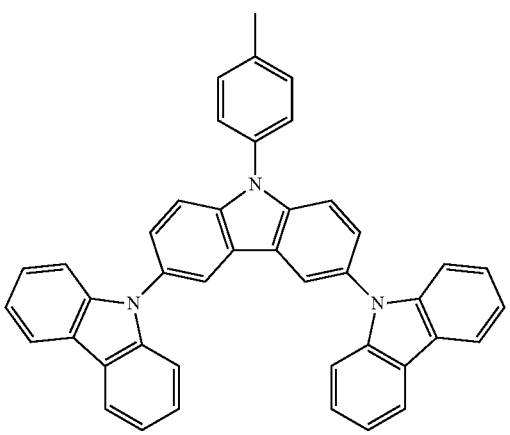
TCzMe
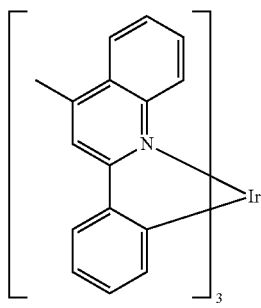
Ir(Mphq)3
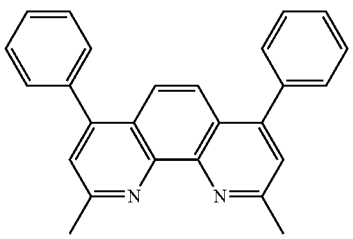
BCP

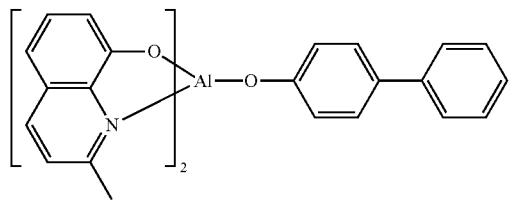

BAIq

TABLE 1

| Ex. | HTL | Voltage $V_{ON}$ | Voltage $V_{10\,mA/cm^2}$ | EQE | At 1000 cd/m² PE (lm/W) | At 1000 cd/m² LE (cd/A) | LT70 (hr) at $L_0$ = 8000 cd/m² |
|---|---|---|---|---|---|---|---|
| Comp. Example 3 | HTM1 | 2.6 | 4.7 | 9.1 | 13.1 | 18.1 | 13 |
| 4 | XVLI | 2.6 | 4.2 | 9.1 | 14.3 | 18.4 | 22 |
| 5 | XVLII | 2.6 | 4.1 | 9.1 | 15.5 | 18.4 | 21 |

From the Device Example 4 and 5 in Table 1, it can be seen that devices containing the inventive compounds have good properties. In particular, devices having the inventive compounds XVLI and XLVII as HTL have lower voltages than Comparative Example 3 containing HTM1. This can be seen in the J-V characteristics in FIG. 2. Using inventive compounds XVLI and XLVII as HTL enables voltages that are respectively 0.5V and 0.6V lower than device using HTM1 at 10 mA/cm² (see Table 1). This in turn enables higher power efficiencies (PE) up to 15.5 lm/W with XVLII compared to 13.1 lm/W with HTM1 i.e. an 18% increase.

From FIG. 3 it is clear that using inventive compounds XVLI and XLVII as HTL has a positive impact on the device stability. Longer lifetimes are obtained with these compounds in comparison with HTM1. Inventive compounds XVLI and XLVII give $LT_{70}$ ($L_0$=8000 cd/m²) of 22 and 21 hrs respectively, which is 60% longer than what HTM1 can deliver ($LT_{70=13}$ hrs).

Without being bound by any theory, in the case of HTM1, residual unreacted vinyl groups may cause problems as they are directly connected to the conjugated core in para position of the triarylamine nitrogen: they will directly interact with the radical cations (holes) accommodated by the materials, which may result in charge trapping and possible degradation mechanism impeding the device stability. In the case of inventive compounds XLVI and XLVII, the improved performance (voltage and lifetime) over HTM1 suggests that having the styrene groups decoupled from the conjugated core prevents unreacted styrene groups to interact with radical cations (holes) limiting their impact on the hole transport and the degradation in the HTL.

This demonstrates the clear advantages of using inventive compounds XLVI and XLVII as HTL.

The invention claimed is:

1. An arylamine compound comprising at least one addition-polymerizable group X selected from the group consisting of

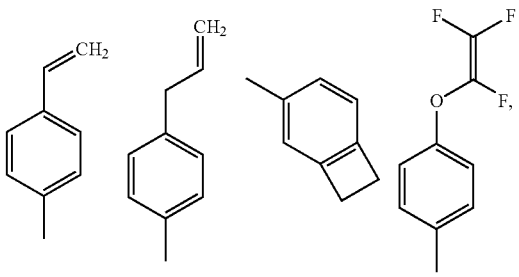

the arylamine compound having general formula (4)

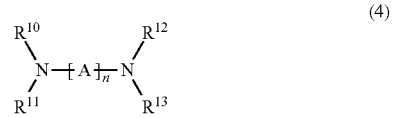

(4)

wherein

A is selected from the group consisting of substituted and unsubstituted 5 to 7 membered aryl and heteroaryl rings, n is 1, 2 or 3, and $R^{10}$ to $R^{13}$ are unsubstituted or substituted $C_5$ to $C_{30}$ aryl or $C_2$ to $C_{30}$ heteroaryl rings, and wherein said addition polymerizable group is attached to at least one of A and $R^{10}$ to $R^{13}$ through a spacer of general formula (1)

(1)

wherein, $R^1$ and $R^2$, independent of one another, each represent a $C_1$-$C_8$ alkyl group or an aryl group of from 5 to 30 carbon atoms, $R^3$ and $R^4$, independent of one another, are hydrogen, a $C_1$ to $C_8$ alkyl group or an aryl group of from 5 to 30 carbon atoms and m is an integer of from 0 to 6.

2. The arylamine compound in accordance with claim 1 wherein $R^1$ and/or $R^2$ is a methyl group.

3. The arylamine compound in accordance with claim 1 wherein m is 0.

4. The arylamine compound in accordance with claim 1 wherein at least one of A and $R^{10}$ to $R^{13}$ is substituted or unsubstituted phenyl or naphthyl.

5. The arylamine compound in accordance with claim 1, wherein the addition-polymerizable group X comprises at least one unsaturated bond.

6. An arylamine compound represented by any one of the following formulae (I)
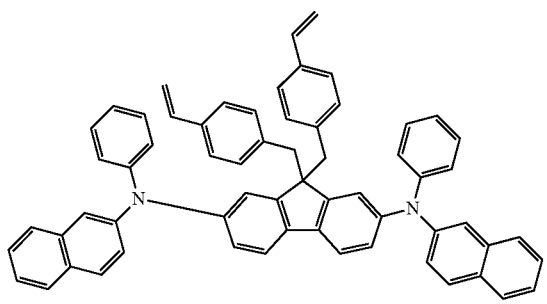
(II)
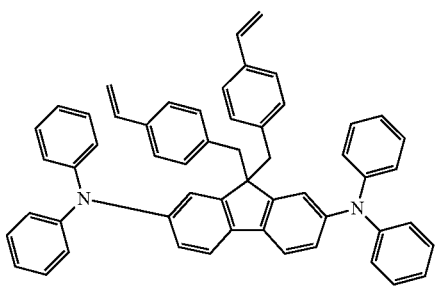
(III)
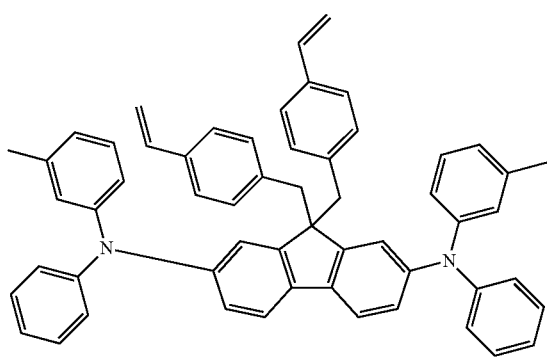
(IV)
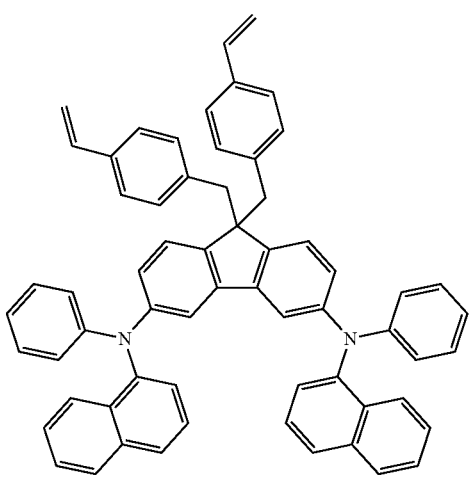
(V)
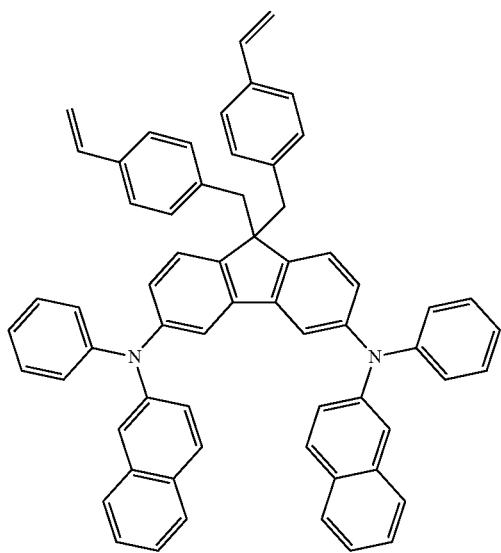
(VI)
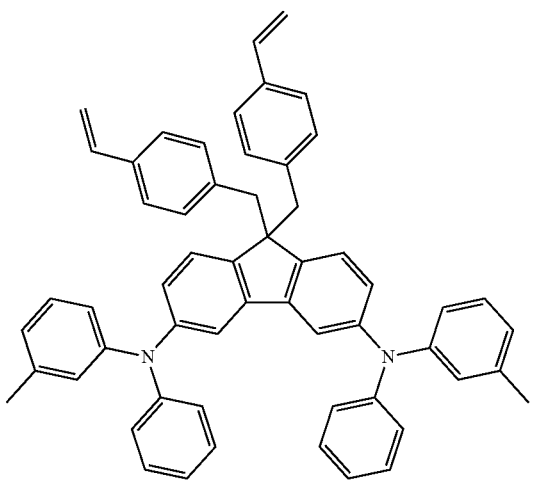

-continued
(VII)
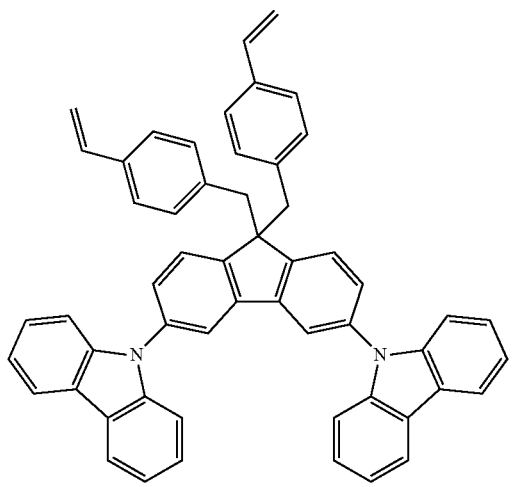
(VIII)
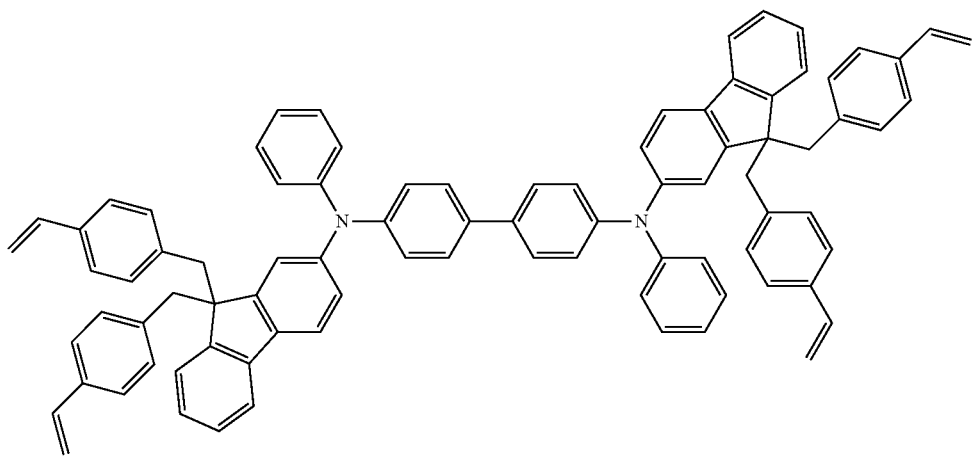
(IX)
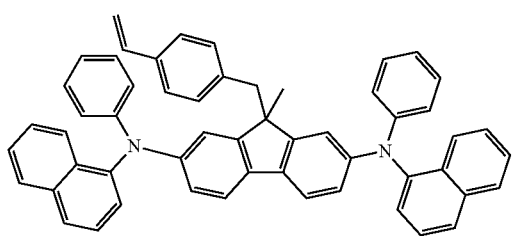
(X)
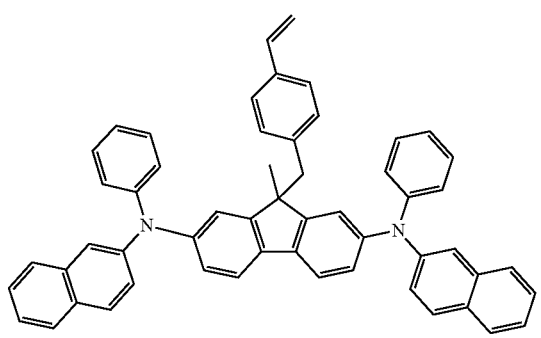

-continued
(XI)
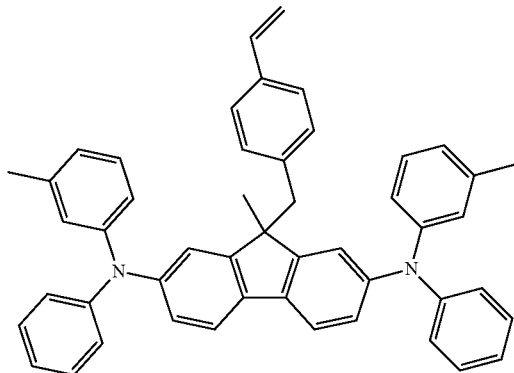
(XII)
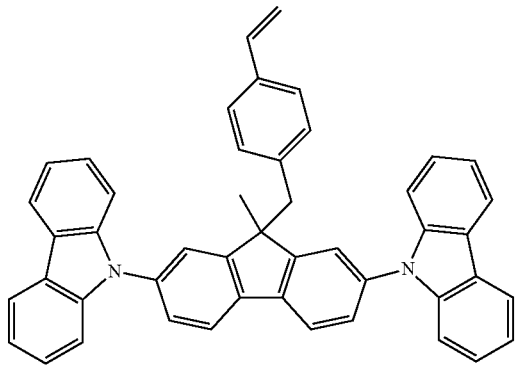
(XIII)
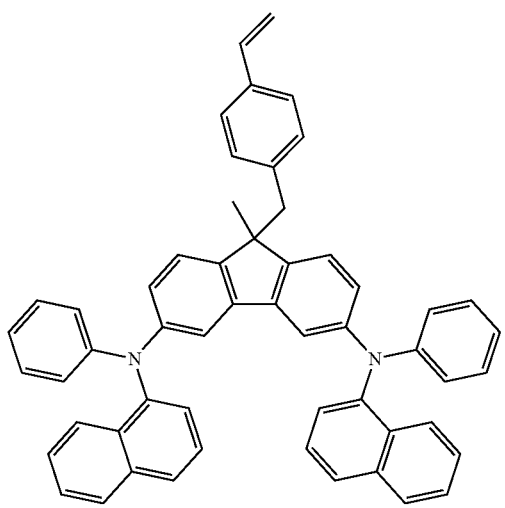
(XIV)
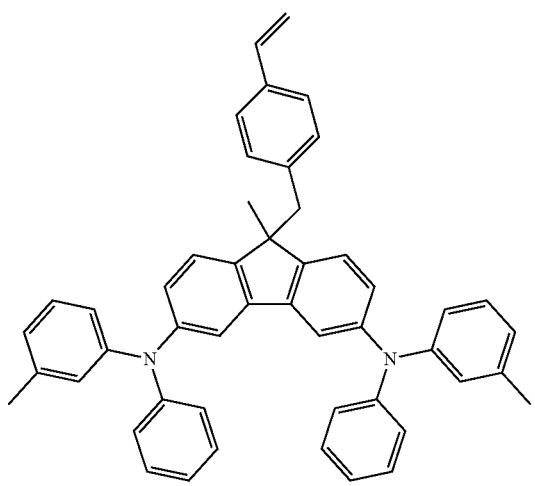
(XV)
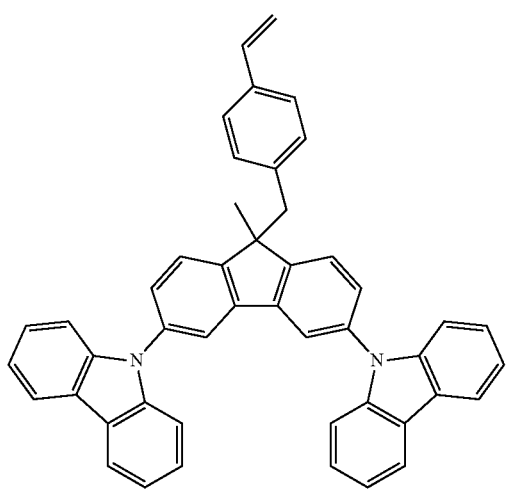

-continued
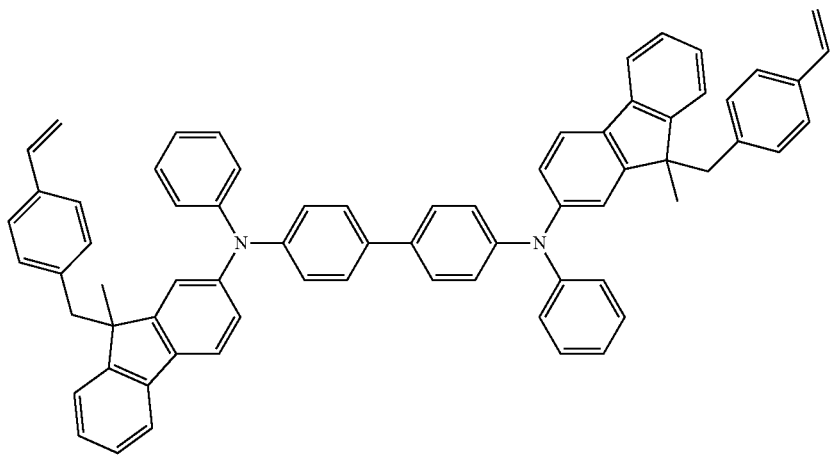
(XVI)
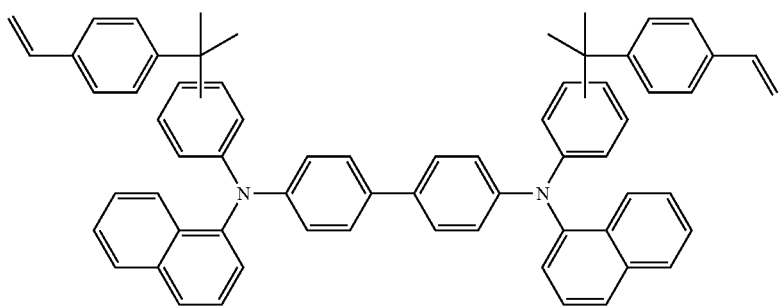
(XVII)
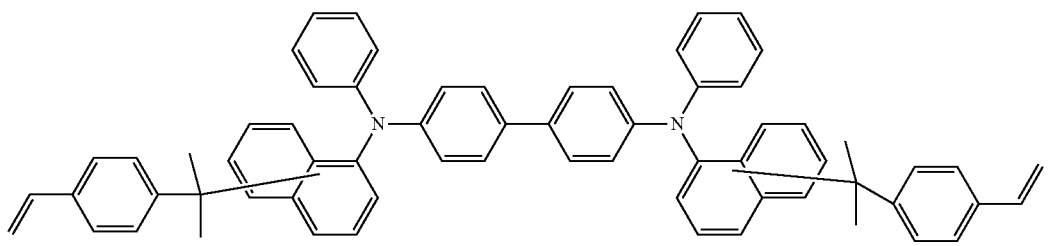
(XIX)
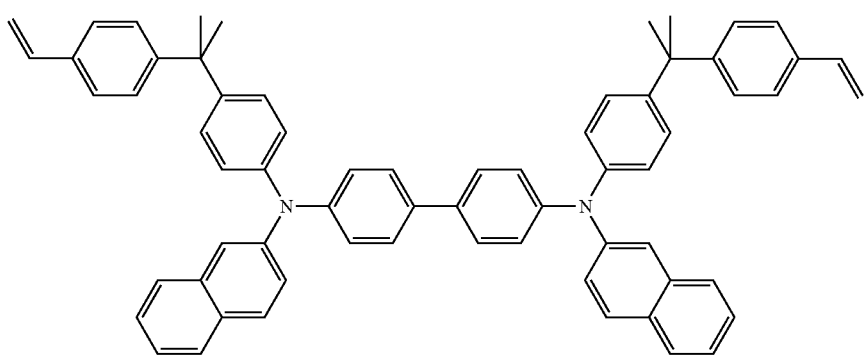
(XX)

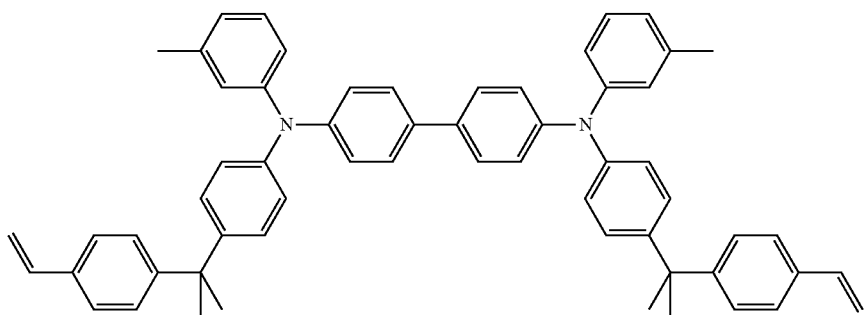
(XXI)
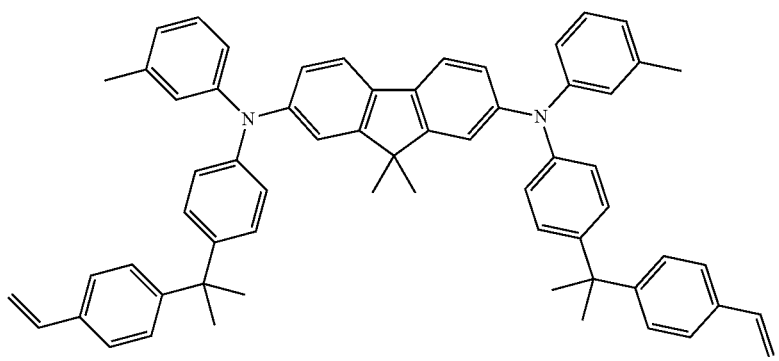
(XXII)
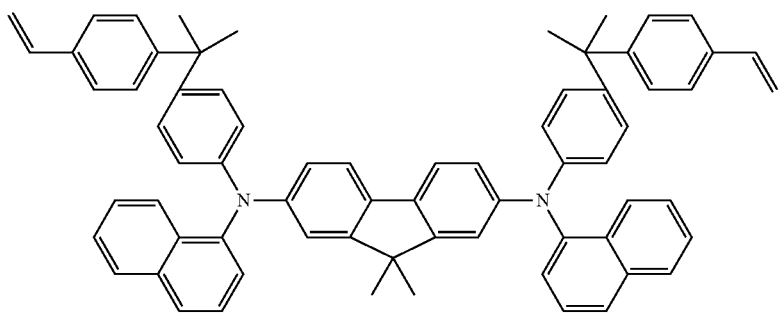
(XXIII)
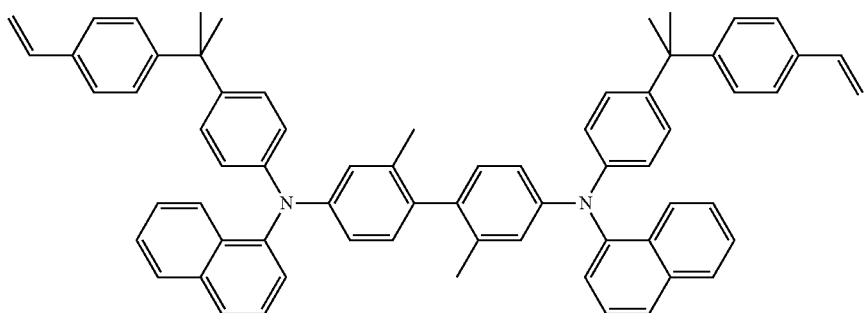
(XXIV)

-continued
(XXV)
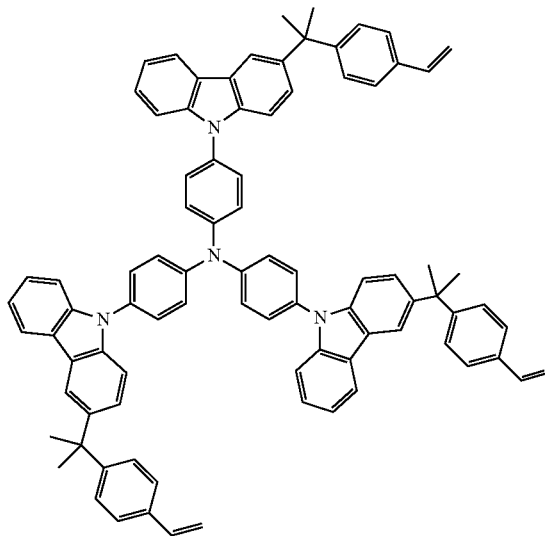
(XXVI)
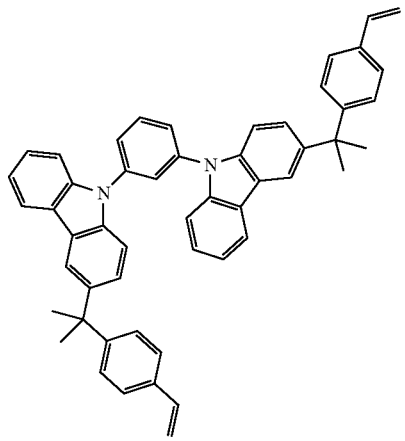
(XXVII)
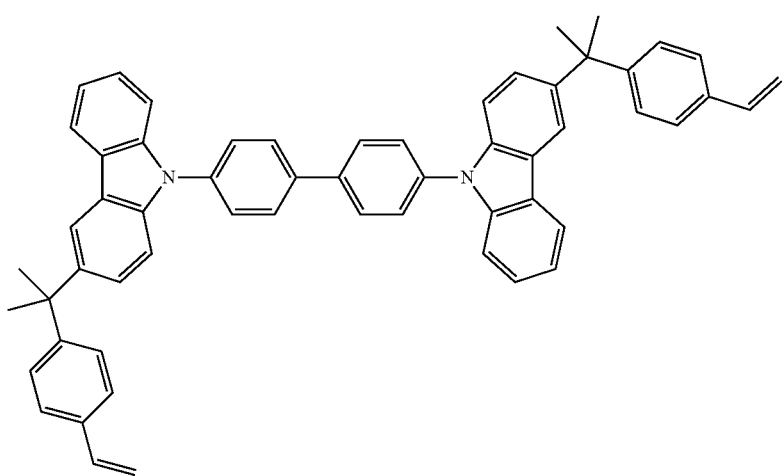
(XVIII)
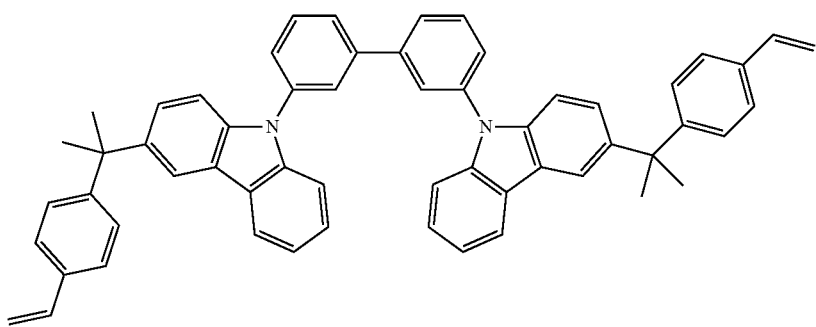

-continued
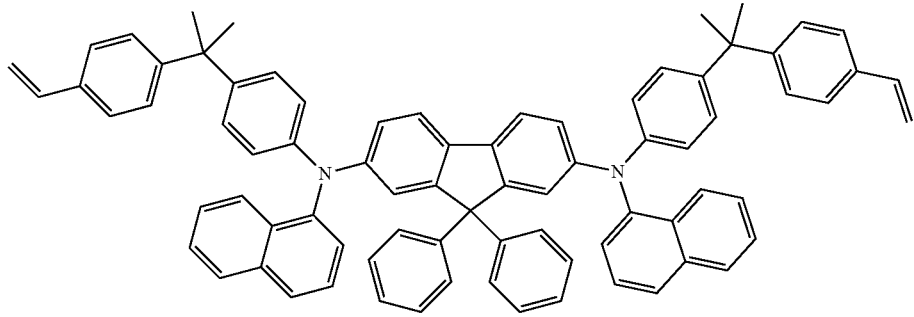
(XXIX)
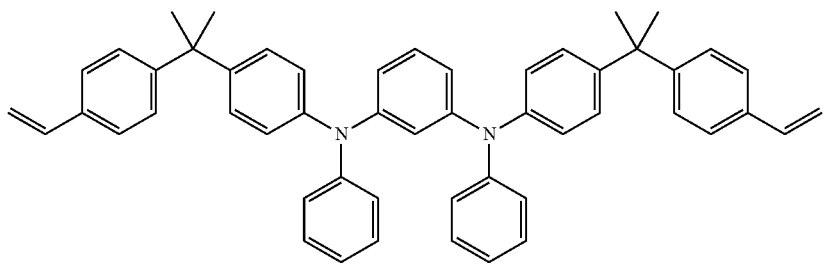
(XXX)
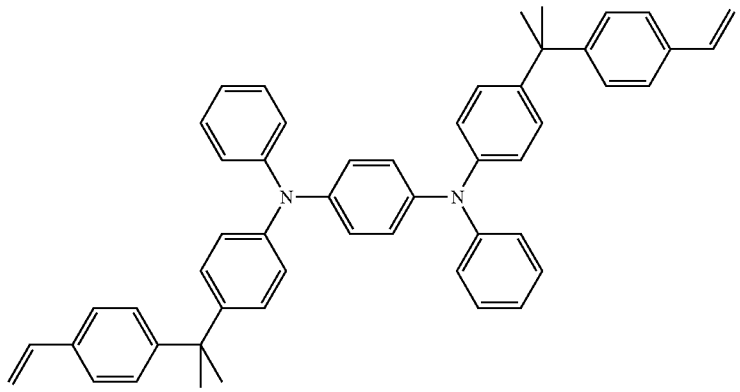
(XXXI)
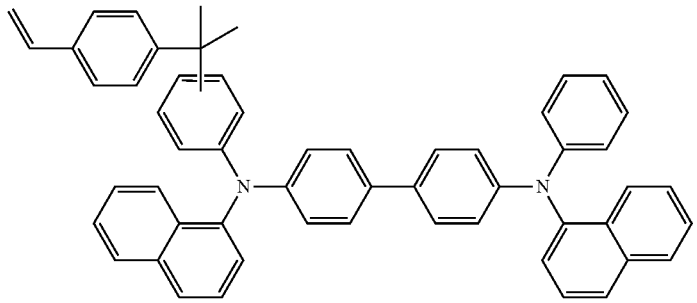
(XXXII)
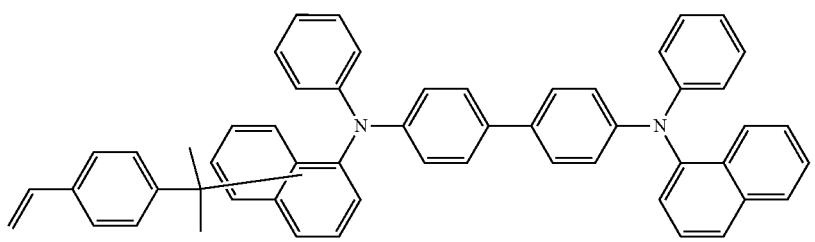
(XXXIII)

-continued
(XXXIV)
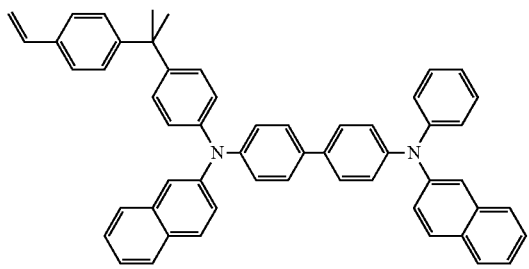
(XXXV)
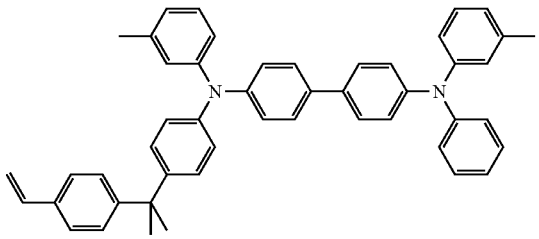
(XXXVI)
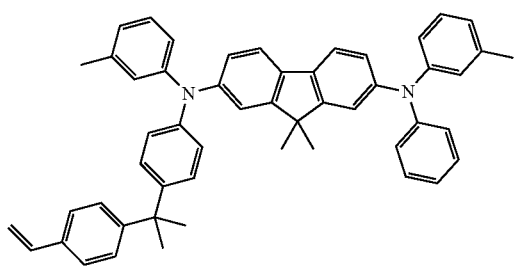
(XXXVII)
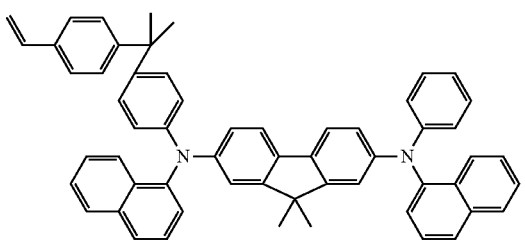
(XXXVIII)
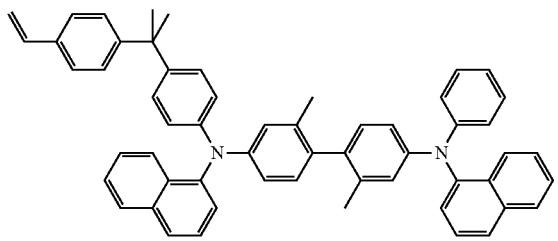
(XXXIX)
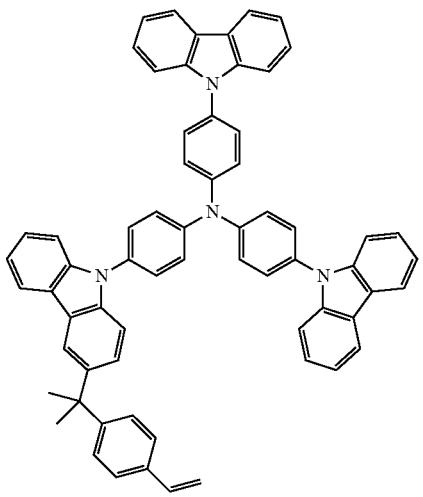
(XL)
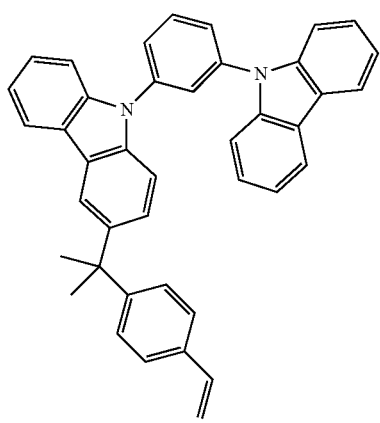
(XLI)
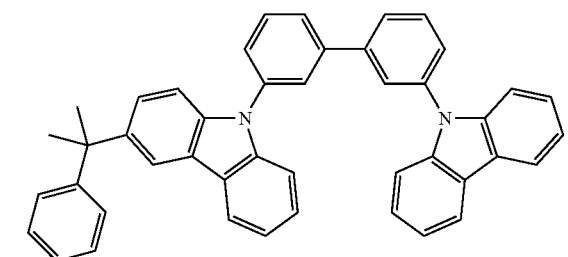

-continued (XLII)
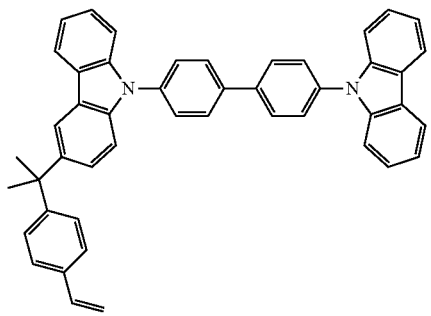

(XLIII)
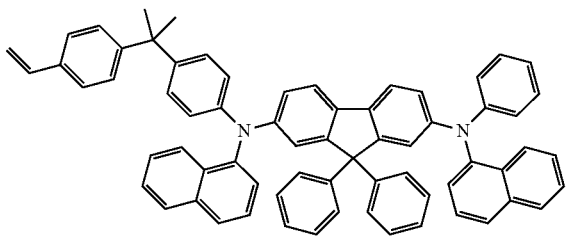

(XLIV)
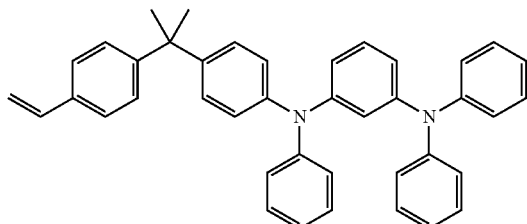

(XLV)
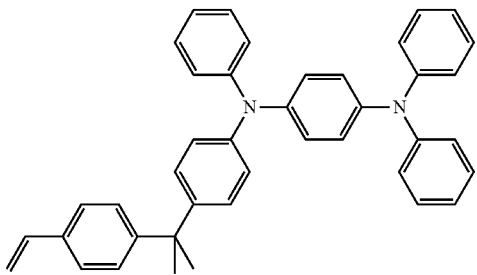

(XLVI)
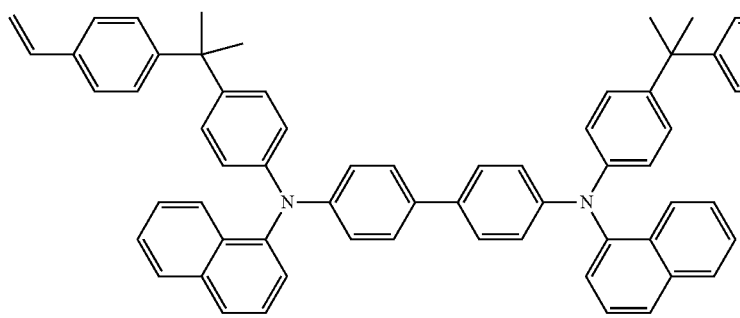

(XLVII)
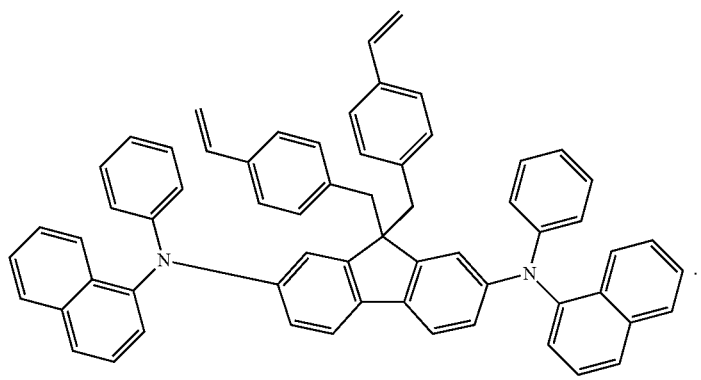

7. An organic electronic device comprising the arylamine compound in accordance with claim 1.

8. The organic electronic device in accordance with claim 7 wherein the device is an organic light emitting diode.

9. Organic light emitting diode comprising a polymer obtained from the arylamine compound in accordance with claim 1.

10. The arylamine compound in accordance with claim 1 wherein m is an integer of from 1 to 3.

11. An organic electronic device comprising the arylamine compound in accordance with claim 6.

12. The organic electronic device in accordance with claim 11 wherein the device is an organic light emitting diode.

13. Organic light emitting diode comprising a polymer obtained from the arylamine compound in accordance with claim 6.

* * * * *